US012790611B2

(12) United States Patent
Antonellis et al.

(10) Patent No.: US 12,790,611 B2
(45) Date of Patent: Nov. 10, 2026

(54) THERAPEUTIC DELIVERY MOIETIES AND USES THEREOF

(71) Applicant: Eli Lilly and Company, Indianapolis, IN (US)

(72) Inventors: Patrick Joseph Antonellis, Indianapolis, IN (US); Gregory Lawrence Lackner, Indianapolis, IN (US); Takako Wilson, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 487 days.

(21) Appl. No.: 18/573,794

(22) PCT Filed: Jun. 22, 2022

(86) PCT No.: PCT/US2022/034500

§ 371 (c)(1),
(2) Date: Dec. 22, 2023

(87) PCT Pub. No.: WO2022/271806

PCT Pub. Date: Dec. 29, 2022

(65) Prior Publication Data

US 2024/0327839 A1 Oct. 3, 2024

Related U.S. Application Data

(60) Provisional application No. 63/214,555, filed on Jun. 24, 2021.

(51) Int. Cl.
*C12N 15/113* (2010.01)
*A61K 47/54* (2017.01)

(52) U.S. Cl.
CPC .......... *C12N 15/113* (2013.01); *A61K 47/549* (2017.08); *C12N 2310/14* (2013.01); *C12N 2310/312* (2013.01); *C12N 2310/315* (2013.01); *C12N 2310/321* (2013.01); *C12N 2310/322* (2013.01); *C12N 2310/351* (2013.01); *C12N 2310/3521* (2013.01); *C12N 2310/3533* (2013.01); *C12N 2330/30* (2013.01)

(58) Field of Classification Search
None
See application file for complete search history.

(56) References Cited

U.S. PATENT DOCUMENTS

| | | | |
|---|---|---|---|
| 8,106,022 | B2 | 1/2012 | Manoharan et al. |
| 8,158,601 | B2 | 4/2012 | Chen et al. |
| 8,313,772 | B2 | 11/2012 | Rozema et al. |
| 8,575,123 | B2 | 11/2013 | Manoharan et al. |
| 9,011,919 | B2 | 4/2015 | Rozema et al. |
| 9,127,276 | B2 | 9/2015 | Prakash et al. |
| 9,181,551 | B2 | 11/2015 | McSwiggen et al. |
| 9,222,091 | B2 | 12/2015 | Manoharan et al. |
| 9,249,179 | B2 | 2/2016 | Hadwiger et al. |
| 9,260,471 | B2 | 2/2016 | Cancilla et al. |
| 9,290,760 | B2 | 3/2016 | Rajeev et al. |
| 9,345,775 | B2 | 5/2016 | Lewis et al. |
| 9,399,775 | B2 | 7/2016 | Rajeev et al. |
| 9,506,030 | B2 | 11/2016 | Bhat |
| 9,540,639 | B2 | 1/2017 | Tellers et al. |
| 9,655,976 | B2 | 5/2017 | Tellers et al. |
| 9,714,421 | B2 | 7/2017 | Prakash et al. |
| 9,732,344 | B2 | 8/2017 | Beigelman et al. |
| 9,796,756 | B2 | 10/2017 | Hadwiger et al. |
| 9,796,974 | B2 | 10/2017 | Rajeev et al. |
| 9,845,546 | B2 | 12/2017 | Nashner |
| 9,962,449 | B2 | 5/2018 | Payne et al. |
| 10,023,861 | B2 | 7/2018 | Prakash et al. |
| 10,077,443 | B2 | 9/2018 | Albaek et al. |
| 10,086,081 | B2 | 10/2018 | Nair et al. |
| 10,131,907 | B2 | 11/2018 | Forst et al. |
| 10,233,448 | B2 | 3/2019 | Maier et al. |
| 10,246,709 | B2 | 4/2019 | Rozema et al. |
| 10,294,474 | B2 | 5/2019 | Li et al. |
| 10,316,316 | B2 | 6/2019 | Lewis et al. |
| 10,351,852 | B2 | 7/2019 | McSwiggen et al. |
| 10,570,169 | B2 | 2/2020 | Seth et al. |
| 10,577,388 | B2 | 3/2020 | Hansen et al. |
| 10,646,582 | B2 | 5/2020 | Monahan et al. |
| 10,689,648 | B2 | 6/2020 | Carr et al. |
| 10,738,308 | B2 | 8/2020 | Chang et al. |
| 10,793,859 | B2 | 10/2020 | Gryaznov et al. |
| 11,840,691 | B2 | 12/2023 | Lu et al. |
| 2011/0269814 | A1 | 11/2011 | Manoharan et al. |
| 2012/0101148 | A1 | 4/2012 | Aking et al. |
| 2014/0371432 | A1 | 12/2014 | Chae et al. |
| 2015/0368642 | A1 | 12/2015 | Albæk et al. |

(Continued)

FOREIGN PATENT DOCUMENTS

| | | | |
|---|---|---|---|
| AU | 2018203979 | A1 | 6/2018 |
| CN | 110218728 | A | 9/2019 |

(Continued)

OTHER PUBLICATIONS

International Search Report and Written Opinion for International Application No. PCT/US2022/034500, Issued by the European Patent Office and mailed on Oct. 6, 2022, 15 pages.

Dehuyser et al., "Synthesis of Novel Mannoside Glycolipid Conjugates for Inhibition of HIC-1 Trans-Infection" *Bioconjugate Chem.*, 2012, 23, 1731-1739.

(Continued)

*Primary Examiner* — Patrick T Lewis

(74) *Attorney, Agent, or Firm* — Robert D. Shereda

(57) ABSTRACT

The present invention relates to novel compounds comprising novel delivery moieties for delivery of oligonucleotides, which are useful in the treatment of disease, suitably diseases of the liver.

28 Claims, No Drawings

Specification includes a Sequence Listing.

(56) References Cited

U.S. PATENT DOCUMENTS

| | | | |
|---|---|---|---|
| 2016/0122761 | A1 | 5/2016 | Prakash et al. |
| 2016/0257961 | A1 | 9/2016 | Bradshaw et al. |
| 2017/0145424 | A1 | 5/2017 | Prakash et al. |
| 2017/0253875 | A1 | 9/2017 | Rozema et al. |
| 2017/0304459 | A1 | 10/2017 | Jadhav et al. |
| 2017/0327524 | A1 | 11/2017 | Albaek et al. |
| 2018/0245083 | A1 | 8/2018 | Beigelman et al. |
| 2019/0046555 | A1 | 2/2019 | Viney et al. |
| 2019/0062749 | A1 | 2/2019 | Zhang |
| 2019/0085331 | A1 | 3/2019 | Hadwiger et al. |
| 2019/0144488 | A1 | 5/2019 | Albaek et al. |
| 2019/0194655 | A1 | 6/2019 | Bradshaw et al. |
| 2019/0224326 | A1 | 7/2019 | Bhat et al. |
| 2019/0256849 | A1 | 8/2019 | Li et al. |
| 2019/0275171 | A1 | 9/2019 | Rigo |
| 2020/0078313 | A1 | 3/2020 | Roy et al. |
| 2020/0224196 | A1 | 7/2020 | Iriyama et al. |
| 2020/0270611 | A1 | 8/2020 | Gryaznov et al. |
| 2020/0338201 | A1 | 10/2020 | Zhang et al. |
| 2020/0369703 | A1 | 11/2020 | Zhang et al. |
| 2020/0392495 | A1 | 12/2020 | Bethge et al. |
| 2020/0392499 | A1 | 12/2020 | Carr et al. |
| 2020/0407724 | A1 | 12/2020 | Heyes et al. |
| 2021/0060168 | A1 | 3/2021 | Rajappan et al. |
| 2021/0087570 | A1 | 3/2021 | Samarsky et al. |
| 2021/0277400 | A1 | 9/2021 | Zhang et al. |

FOREIGN PATENT DOCUMENTS

| | | | |
|---|---|---|---|
| EP | 3019200 | A1 | 5/2016 |
| EP | 3443092 | A1 | 2/2019 |
| EP | 3544617 | A1 | 10/2019 |
| EP | 3677588 | A1 | 7/2020 |
| EP | 3763815 | A1 | 1/2021 |
| EP | 3790557 | A2 | 3/2021 |
| EP | 3453762 | B1 | 4/2021 |
| EP | 3808846 | A1 | 4/2021 |
| WO | 2011163121 | A1 | 12/2011 |
| WO | 2012083185 | A2 | 6/2012 |
| WO | 2014179446 | A2 | 11/2014 |
| WO | 2014179620 | A1 | 11/2014 |
| WO | 2015051318 | A1 | 4/2015 |
| WO | 2015168618 | A2 | 11/2015 |
| WO | 2018044350 | A1 | 3/2018 |
| WO | 2018067900 | A1 | 4/2018 |
| WO | 2019105403 | A1 | 6/2019 |
| WO | 2019105404 | A1 | 6/2019 |
| WO | 2019105418 | A1 | 6/2019 |
| WO | 2019128611 | A1 | 7/2019 |
| WO | 2019/232255 | A1 | 12/2019 |
| WO | 2020044186 | A2 | 3/2020 |
| WO | 2020063198 | A1 | 4/2020 |
| WO | 2020093061 | A1 | 5/2020 |
| WO | 2020097044 | A1 | 5/2020 |
| WO | 2020104649 | A2 | 5/2020 |
| WO | 2020/132564 | A1 | 6/2020 |
| WO | 2020123410 | A1 | 6/2020 |
| WO | 2020/191183 | A1 | 9/2020 |
| WO | 2020172755 | A1 | 9/2020 |
| WO | 2020236600 | A1 | 11/2020 |
| WO | 2021/030778 | A1 | 2/2021 |
| WO | 2021032777 | A1 | 2/2021 |
| WO | 2021/049504 | A1 | 3/2021 |
| WO | 2021037205 | A1 | 3/2021 |
| WO | 2021071858 | A1 | 4/2021 |

OTHER PUBLICATIONS

Rensen et al., "Design and Synthesis of Novel N-Acetylgalactosamine-Terminated Glycolipids for Targeting of Lipoproteins to the Hepatic Asialoglycoprotein Receptor" *J. Med. Chem.*, 2004, 47, 5798-5808.

Schaeffer et al., "Dynamic Micelles of Mannoside Glycolipids are more Efficient than Polymers for Inhibiting HIV-1 trans-Infection" *Bioconjugate Chem.*, 2013, 24, 1813-1823.

Sharma et al., "Novel Cluster and Monomer-Based GalNAc Structures Induce Effective Uptake of siRNAs in Vitro and in Vivo" *Bioconjugate Chem.*, 2018, 29, 2478-2488.

SEQUENCE LISTING

<160> NUMBER OF SEQ ID NOS: 6

<210> SEQ ID NO 1
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(1)
<223> OTHER INFORMATION: 2'-OMe modified nucleotide with a
3'-phosphorothioate linkage and a 5'-phosphate substitution
<220> FEATURE:
<221> NAME/KEY: misc_feature
<222> LOCATION: (2)..(2)
<223> OTHER INFORMATION: 2'-F modified nucleotide with a
3'-phosphorothioate linkage
<220> FEATURE:
<221> NAME/KEY: misc_feature
<222> LOCATION: (3)..(3)
<223> OTHER INFORMATION: 2'-OMe modified nucleotide
<220> FEATURE:
<221> NAME/KEY: misc_feature
<222> LOCATION: (4)..(4)
<223> OTHER INFORMATION: 2'-OMe modified nucleotide
<220> FEATURE:
<221> NAME/KEY: misc_feature
<222> LOCATION: (5)..(5)
<223> OTHER INFORMATION: 2'-OMe modified nucleotide
<220> FEATURE:
<221> NAME/KEY: misc_feature
<222> LOCATION: (6)..(6)
<223> OTHER INFORMATION: 2'-F modified nucleotide
<220> FEATURE:
<221> NAME/KEY: misc_feature
<222> LOCATION: (7)..(7)
<223> OTHER INFORMATION: 2'-OMe modified nucleotide
<220> FEATURE:
<221> NAME/KEY: misc_feature
<222> LOCATION: (8)..(8)
<223> OTHER INFORMATION: 2'-OMe modified nucleotide
<220> FEATURE:
<221> NAME/KEY: misc_feature
<222> LOCATION: (9)..(9)
<223> OTHER INFORMATION: 2'-OMe modified nucleotide
<220> FEATURE:
<221> NAME/KEY: misc_feature
<222> LOCATION: (10)..(10)
<223> OTHER INFORMATION: 2'-OMe modified nucleotide
<220> FEATURE:
<221> NAME/KEY: misc_feature
<222> LOCATION: (11)..(11)
<223> OTHER INFORMATION: 2'-OMe modified nucleotide
<220> FEATURE:
<221> NAME/KEY: misc_feature
<222> LOCATION: (12)..(12)
<223> OTHER INFORMATION: 2'-OMe modified nucleotide
<220> FEATURE:
<221> NAME/KEY: misc_feature
<222> LOCATION: (13)..(13)
<223> OTHER INFORMATION: 2'-OMe modified nucleotide
<220> FEATURE:
<221> NAME/KEY: misc_feature
<222> LOCATION: (14)..(14)
<223> OTHER INFORMATION: 2'-F modified nucleotide
<220> FEATURE:
<221> NAME/KEY: misc_feature
<222> LOCATION: (15)..(15)
<223> OTHER INFORMATION: 2'-OMe modified nucleotide
<220> FEATURE:
<221> NAME/KEY: misc_feature
<222> LOCATION: (16)..(16)
<223> OTHER INFORMATION: 2'-F modified nucleotide
<220> FEATURE:
<221> NAME/KEY: misc_feature
<222> LOCATION: (17)..(17)
<223> OTHER INFORMATION: 2'-OMe modified nucleotide
<220> FEATURE:
<221> NAME/KEY: misc_feature
<222> LOCATION: (18)..(18)
<223> OTHER INFORMATION: 2'-OMe modified nucleotide
<220> FEATURE:

-continued

<221> NAME/KEY: misc_feature
<222> LOCATION: (19)..(19)
<223> OTHER INFORMATION: 2'-OMe modified nucleotide
<220> FEATURE:
<221> NAME/KEY: misc_feature
<222> LOCATION: (20)..(20)
<223> OTHER INFORMATION: 2'-OMe modified nucleotide
<220> FEATURE:
<221> NAME/KEY: misc_feature
<222> LOCATION: (21)..(21)
<223> OTHER INFORMATION: 2'-OMe modified nucleotide with a 3'-phosphorothioate linkage
<220> FEATURE:
<221> NAME/KEY: misc_feature
<222> LOCATION: (22)..(22)
<223> OTHER INFORMATION: 2'-OMe modified nucleotide with a 3'-phosphorothioate linkage
<220> FEATURE:
<221> NAME/KEY: misc_feature
<222> LOCATION: (23)..(23)
<223> OTHER INFORMATION: 2'-OMe modified nucleotide

<400> SEQUENCE: 1
auaaaaucua cagucauagg aau 23

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(1)
<223> OTHER INFORMATION: 2'-OMe modified nucleotide with a 3'-phosphorothioate linkage
<220> FEATURE:
<221> NAME/KEY: misc_feature
<222> LOCATION: (2)..(2)
<223> OTHER INFORMATION: 2'-OMe modified nucleotide with a 3'-phosphorothioate linkage
<220> FEATURE:
<221> NAME/KEY: misc_feature
<222> LOCATION: (3)..(3)
<223> OTHER INFORMATION: 2'-OMe modified nucleotide
<220> FEATURE:
<221> NAME/KEY: misc_feature
<222> LOCATION: (4)..(4)
<223> OTHER INFORMATION: 2'-OMe modified nucleotide
<220> FEATURE:
<221> NAME/KEY: misc_feature
<222> LOCATION: (5)..(5)
<223> OTHER INFORMATION: 2'-OMe modified nucleotide
<220> FEATURE:
<221> NAME/KEY: misc_feature
<222> LOCATION: (6)..(6)
<223> OTHER INFORMATION: 2'-OMe modified nucleotide
<220> FEATURE:
<221> NAME/KEY: misc_feature
<222> LOCATION: (7)..(7)
<223> OTHER INFORMATION: 2'-F modified nucleotide
<220> FEATURE:
<221> NAME/KEY: misc_feature
<222> LOCATION: (8)..(8)
<223> OTHER INFORMATION: 2'-OMe modified nucleotide
<220> FEATURE:
<221> NAME/KEY: misc_feature
<222> LOCATION: (9)..(9)
<223> OTHER INFORMATION: 2'-F modified nucleotide
<220> FEATURE:
<221> NAME/KEY: misc_feature
<222> LOCATION: (10)..(10)
<223> OTHER INFORMATION: 2'-F modified nucleotide
<220> FEATURE:
<221> NAME/KEY: misc_feature
<222> LOCATION: (11)..(11)

<223> OTHER INFORMATION: 2'-F modified nucleotide
<220> FEATURE:
<221> NAME/KEY: misc_feature
<222> LOCATION: (12)..(12)
<223> OTHER INFORMATION: 2'-OMe modified nucleotide
<220> FEATURE:
<221> NAME/KEY: misc_feature
<222> LOCATION: (13)..(13)
<223> OTHER INFORMATION: 2'-OMe modified nucleotide
<220> FEATURE:
<221> NAME/KEY: misc_feature
<222> LOCATION: (14)..(14)
<223> OTHER INFORMATION: 2'-OMe modified nucleotide
<220> FEATURE:
<221> NAME/KEY: misc_feature
<222> LOCATION: (15)..(15)
<223> OTHER INFORMATION: 2'-OMe modified nucleotide
<220> FEATURE:
<221> NAME/KEY: misc_feature
<222> LOCATION: (16)..(16)
<223> OTHER INFORMATION: 2'-OMe modified nucleotide
<220> FEATURE:
<221> NAME/KEY: misc_feature
<222> LOCATION: (17)..(17)
<223> OTHER INFORMATION: 2'-OMe modified nucleotide
<220> FEATURE:
<221> NAME/KEY: misc_feature
<222> LOCATION: (18)..(18)
<223> OTHER INFORMATION: 2'-OMe modified nucleotide
<220> FEATURE:
<221> NAME/KEY: misc_feature
<222> LOCATION: (19)..(19)
<223> OTHER INFORMATION: 2'-OMe modified nucleotide with a
3'-phosphorothioate linkage
<220> FEATURE:
<221> NAME/KEY: misc_feature
<222> LOCATION: (20)..(20)
<223> OTHER INFORMATION: 2'-OMe modified nucleotide with a
3'-phosphorothioate linkage
<220> FEATURE:
<221> NAME/KEY: misc_feature
<222> LOCATION: (21)..(21)
<223> OTHER INFORMATION: 2'-OMe modified nucleotide

<400> SEQUENCE: 2
uccuaugacu guagauuuua u 21

<210> SEQ ID NO 3
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(1)
<223> OTHER INFORMATION: 2'-OMe modified nucleotide with a
3'-phosphorothioate linkage and
a 5'-phosphate substitution
<220> FEATURE:
<221> NAME/KEY: misc_feature
<222> LOCATION: (2)..(2)
<223> OTHER INFORMATION: 2'-F modified nucleotide with a
3'-phosphorothioate linkage
<220> FEATURE:
<221> NAME/KEY: misc_feature
<222> LOCATION: (3)..(3)
<223> OTHER INFORMATION: 2'-OMe modified nucleotide
<220> FEATURE:
<221> NAME/KEY: misc_feature
<222> LOCATION: (4)..(4)
<223> OTHER INFORMATION: 2'-OMe modified nucleotide
<220> FEATURE:
<221> NAME/KEY: misc_feature
<222> LOCATION: (5)..(5)
<223> OTHER INFORMATION: 2'-OMe modified nucleotide -continued
<220> FEATURE:
<221> NAME/KEY: misc_feature
<222> LOCATION: (6)..(6)
<223> OTHER INFORMATION: 2'-F modified nucleotide
<220> FEATURE:
<221> NAME/KEY: misc_feature
<222> LOCATION: (7)..(7)
<223> OTHER INFORMATION: 2'-OMe modified nucleotide
<220> FEATURE:
<221> NAME/KEY: misc_feature
<222> LOCATION: (8)..(8)
<223> OTHER INFORMATION: 2'-OMe modified nucleotide
<220> FEATURE:
<221> NAME/KEY: misc_feature
<222> LOCATION: (9)..(9)
<223> OTHER INFORMATION: 2'-OMe modified nucleotide
<220> FEATURE:
<221> NAME/KEY: misc_feature
<222> LOCATION: (10)..(10)
<223> OTHER INFORMATION: 2'-OMe modified nucleotide
<220> FEATURE:
<221> NAME/KEY: misc_feature
<222> LOCATION: (11)..(11)
<223> OTHER INFORMATION: 2'-OMe modified nucleotide
<220> FEATURE:
<221> NAME/KEY: misc_feature
<222> LOCATION: (12)..(12)
<223> OTHER INFORMATION: 2'-OMe modified nucleotide
<220> FEATURE:
<221> NAME/KEY: misc_feature
<222> LOCATION: (13)..(13)
<223> OTHER INFORMATION: 2'-OMe modified nucleotide
<220> FEATURE:
<221> NAME/KEY: misc_feature
<222> LOCATION: (14)..(14)
<223> OTHER INFORMATION: 2'-F modified nucleotide
<220> FEATURE:
<221> NAME/KEY: misc_feature
<222> LOCATION: (15)..(15)
<223> OTHER INFORMATION: 2'-OMe modified nucleotide
<220> FEATURE:
<221> NAME/KEY: misc_feature
<222> LOCATION: (16)..(16)
<223> OTHER INFORMATION: 2'-F modified nucleotide
<220> FEATURE:
<221> NAME/KEY: misc_feature
<222> LOCATION: (17)..(17)
<223> OTHER INFORMATION: 2'-OMe modified nucleotide
<220> FEATURE:
<221> NAME/KEY: misc_feature
<222> LOCATION: (18)..(18)
<223> OTHER INFORMATION: 2'-OMe modified nucleotide
<220> FEATURE:
<221> NAME/KEY: misc_feature
<222> LOCATION: (19)..(19)
<223> OTHER INFORMATION: 2'-OMe modified nucleotide
<220> FEATURE:
<221> NAME/KEY: misc_feature
<222> LOCATION: (20)..(20)
<223> OTHER INFORMATION: 2'-OMe modified nucleotide
<220> FEATURE:
<221> NAME/KEY: misc_feature
<222> LOCATION: (21)..(21)
<223> OTHER INFORMATION: 2'-OMe modified nucleotide with a
3'-phosphorothioate linkage
<220> FEATURE:
<221> NAME/KEY: misc_feature
<222> LOCATION: (22)..(22)
<223> OTHER INFORMATION: 2'-OMe modified nucleotide with a
3'-phosphorothioate linkage
<220> FEATURE:
<221> NAME/KEY: misc_feature
<222> LOCATION: (23)..(23)
<223> OTHER INFORMATION: 2'-OMe modified nucleotide

<400> SEQUENCE: 3
acguagguca agauauccac ugg 23

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(1)
<223> OTHER INFORMATION: 2'-OMe modified nucleotide with a
3'-phosphorothioate linkage
<220> FEATURE:
<221> NAME/KEY: misc_feature
<222> LOCATION: (2)..(2)
<223> OTHER INFORMATION: 2'-OMe modified nucleotide with a
3'-phosphorothioate linkage
<220> FEATURE:
<221> NAME/KEY: misc_feature
<222> LOCATION: (3)..(3)
<223> OTHER INFORMATION: 2'-OMe modified nucleotide
<220> FEATURE:
<221> NAME/KEY: misc_feature
<222> LOCATION: (4)..(4)
<223> OTHER INFORMATION: 2'-OMe modified nucleotide
<220> FEATURE:
<221> NAME/KEY: misc_feature
<222> LOCATION: (5)..(5)
<223> OTHER INFORMATION: 2'-OMe modified nucleotide
<220> FEATURE:
<221> NAME/KEY: misc_feature
<222> LOCATION: (6)..(6)
<223> OTHER INFORMATION: 2'-OMe modified nucleotide
<220> FEATURE:
<221> NAME/KEY: misc_feature
<222> LOCATION: (7)..(7)
<223> OTHER INFORMATION: 2'-F modified nucleotide
<220> FEATURE:
<221> NAME/KEY: misc_feature
<222> LOCATION: (8)..(8)
<223> OTHER INFORMATION: 2'-OMe modified nucleotide
<220> FEATURE:
<221> NAME/KEY: misc_feature
<222> LOCATION: (9)..(9)
<223> OTHER INFORMATION: 2'-F modified nucleotide
<220> FEATURE:
<221> NAME/KEY: misc_feature
<222> LOCATION: (10)..(10)
<223> OTHER INFORMATION: 2'-F modified nucleotide
<220> FEATURE:
<221> NAME/KEY: misc_feature
<222> LOCATION: (11)..(11)
<223> OTHER INFORMATION: 2'-F modified nucleotide
<220> FEATURE:
<221> NAME/KEY: misc_feature
<222> LOCATION: (12)..(12)
<223> OTHER INFORMATION: 2'-OMe modified nucleotide
<220> FEATURE:
<221> NAME/KEY: misc_feature
<222> LOCATION: (13)..(13)
<223> OTHER INFORMATION: 2'-OMe modified nucleotide
<220> FEATURE:
<221> NAME/KEY: misc_feature
<222> LOCATION: (14)..(14)
<223> OTHER INFORMATION: 2'-OMe modified nucleotide
<220> FEATURE:
<221> NAME/KEY: misc_feature
<222> LOCATION: (15)..(15)
<223> OTHER INFORMATION: 2'-OMe modified nucleotide
<220> FEATURE:
<221> NAME/KEY: misc_feature
<222> LOCATION: (16)..(16)
<223> OTHER INFORMATION: 2'-OMe modified nucleotide
<220> FEATURE:
<221> NAME/KEY: misc_feature
<222> LOCATION: (17)..(17)
<223> OTHER INFORMATION: 2'-OMe modified nucleotide
<220> FEATURE:

-continued

<221> NAME/KEY: misc_feature
<222> LOCATION: (18)..(18)
<223> OTHER INFORMATION: 2'-OMe modified nucleotide
<220> FEATURE:
<221> NAME/KEY: misc_feature
<222> LOCATION: (19)..(19)
<223> OTHER INFORMATION: 2'-OMe modified nucleotide with a
      3'-phosphorothioate linkage
<220> FEATURE:
<221> NAME/KEY: misc_feature
<222> LOCATION: (20)..(20)
<223> OTHER INFORMATION: 2'-OMe modified nucleotide with a
      3'-phosphorothioate linkage
<220> FEATURE:
<221> NAME/KEY: misc_feature
<222> LOCATION: (21)..(21)
<223> OTHER INFORMATION: 2'-OMe modified nucleotide

<400> SEQUENCE: 4
aguggauauc uugaccuacg u 21

<210> SEQ ID NO 5
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: 2'-OMe modified nucleotide with a
      3'-phosphorothioate linkage and a 5'-phosphate substitution
<220> FEATURE:
<221> NAME/KEY: misc_feature
<222> LOCATION: (2)..(2)
<223> OTHER INFORMATION: 2'-F modified nucleotide with a
      3'-phosphorothioate linkage
<220> FEATURE:
<221> NAME/KEY: misc_feature
<222> LOCATION: (3)..(3)
<223> OTHER INFORMATION: 2'-OMe modified nucleotide
<220> FEATURE:
<221> NAME/KEY: misc_feature
<222> LOCATION: (4)..(4)
<223> OTHER INFORMATION: 2'-OMe modified nucleotide
<220> FEATURE:
<221> NAME/KEY: misc_feature
<222> LOCATION: (5)..(5)
<223> OTHER INFORMATION: 2'-OMe modified nucleotide
<220> FEATURE:
<221> NAME/KEY: misc_feature
<222> LOCATION: (6)..(6)
<223> OTHER INFORMATION: 2'-F modified nucleotide
<220> FEATURE:
<221> NAME/KEY: misc_feature
<222> LOCATION: (7)..(7)
<223> OTHER INFORMATION: 2'-OMe modified nucleotide
<220> FEATURE:
<221> NAME/KEY: misc_feature
<222> LOCATION: (8)..(8)
<223> OTHER INFORMATION: 2'-OMe modified nucleotide
<220> FEATURE:
<221> NAME/KEY: misc_feature
<222> LOCATION: (9)..(9)
<223> OTHER INFORMATION: 2'-OMe modified nucleotide
<220> FEATURE:
<221> NAME/KEY: misc_feature
<222> LOCATION: (10)..(10)
<223> OTHER INFORMATION: 2'-OMe modified nucleotide
<220> FEATURE:
<221> NAME/KEY: misc_feature
<222> LOCATION: (11)..(11)
<223> OTHER INFORMATION: 2'-OMe modified nucleotide
<220> FEATURE:
<221> NAME/KEY: misc_feature
<222> LOCATION: (12)..(12)

<223> OTHER INFORMATION: 2'-OMe modified nucleotide
<220> FEATURE:
<221> NAME/KEY: misc_feature
<222> LOCATION: (13)..(13)
<223> OTHER INFORMATION: 2'-OMe modified nucleotide
<220> FEATURE:
<221> NAME/KEY: misc_feature
<222> LOCATION: (14)..(14)
<223> OTHER INFORMATION: 2'-F modified nucleotide
<220> FEATURE:
<221> NAME/KEY: misc_feature
<222> LOCATION: (15)..(15)
<223> OTHER INFORMATION: 2'-OMe modified nucleotide
<220> FEATURE:
<221> NAME/KEY: misc_feature
<222> LOCATION: (16)..(16)
<223> OTHER INFORMATION: 2'-F modified nucleotide
<220> FEATURE:
<221> NAME/KEY: misc_feature
<222> LOCATION: (17)..(17)
<223> OTHER INFORMATION: 2'-OMe modified nucleotide
<220> FEATURE:
<221> NAME/KEY: misc_feature
<222> LOCATION: (18)..(18)
<223> OTHER INFORMATION: 2'-OMe modified nucleotide
<220> FEATURE:
<221> NAME/KEY: misc_feature
<222> LOCATION: (19)..(19)
<223> OTHER INFORMATION: 2'-OMe modified nucleotide
<220> FEATURE:
<221> NAME/KEY: misc_feature
<222> LOCATION: (20)..(20)
<223> OTHER INFORMATION: 2'-OMe modified nucleotide
<220> FEATURE:
<221> NAME/KEY: misc_feature
<222> LOCATION: (21)..(21)
<223> OTHER INFORMATION: 2'-OMe modified nucleotide with a
      3'-phosphorothioate linkage
<220> FEATURE:
<221> NAME/KEY: misc_feature
<222> LOCATION: (22)..(22)
<223> OTHER INFORMATION: 2'-OMe modified nucleotide with a
      3'-phosphorothioate linkage
<220> FEATURE:
<221> NAME/KEY: misc_feature
<222> LOCATION: (23)..(23)
<223> OTHER INFORMATION: 2'-OMe modified nucleotide

<400> SEQUENCE: 5
aauaaggagg uacucaacuu guu 23

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: 2'-OMe modified nucleotide with a
      3'-phosphorothioate linkage
<220> FEATURE:
<221> NAME/KEY: misc_feature
<222> LOCATION: (2)..(2)
<223> OTHER INFORMATION: 2'-OMe modified nucleotide with a 3'-
      phosphorothioate linkage
<220> FEATURE:
<221> NAME/KEY: misc_feature
<222> LOCATION: (3)..(3)
<223> OTHER INFORMATION: 2'-OMe modified nucleotide
<220> FEATURE:
<221> NAME/KEY: misc_feature
<222> LOCATION: (4)..(4)
<223> OTHER INFORMATION: 2'-OMe modified nucleotide
<220> FEATURE:

<221> NAME/KEY: misc_feature
<222> LOCATION: (5)..(5)
<223> OTHER INFORMATION: 2'-OMe modified nucleotide
<220> FEATURE:
<221> NAME/KEY: misc_feature
<222> LOCATION: (6)..(6)
<223> OTHER INFORMATION: 2'-OMe modified nucleotide
<220> FEATURE:
<221> NAME/KEY: misc_feature
<222> LOCATION: (7)..(7)
<223> OTHER INFORMATION: 2'-F modified nucleotide
<220> FEATURE:
<221> NAME/KEY: misc_feature
<222> LOCATION: (8)..(8)
<223> OTHER INFORMATION: 2'-OMe modified nucleotide
<220> FEATURE:
<221> NAME/KEY: misc_feature
<222> LOCATION: (9)..(9)
<223> OTHER INFORMATION: 2'-F modified nucleotide
<220> FEATURE:
<221> NAME/KEY: misc_feature
<222> LOCATION: (10)..(10)
<223> OTHER INFORMATION: 2'-F modified nucleotide
<220> FEATURE:
<221> NAME/KEY: misc_feature
<222> LOCATION: (11)..(11)
<223> OTHER INFORMATION: 2'-F modified nucleotide
<220> FEATURE:
<221> NAME/KEY: misc_feature
<222> LOCATION: (12)..(12)
<223> OTHER INFORMATION: 2'-OMe modified nucleotide
<220> FEATURE:
<221> NAME/KEY: misc_feature
<222> LOCATION: (13)..(13)
<223> OTHER INFORMATION: 2'-OMe modified nucleotide
<220> FEATURE:
<221> NAME/KEY: misc_feature
<222> LOCATION: (14)..(14)
<223> OTHER INFORMATION: 2'-OMe modified nucleotide
<220> FEATURE:
<221> NAME/KEY: misc_feature
<222> LOCATION: (15)..(15)
<223> OTHER INFORMATION: 2'-OMe modified nucleotide
<220> FEATURE:
<221> NAME/KEY: misc_feature
<222> LOCATION: (16)..(16)
<223> OTHER INFORMATION: 2'-OMe modified nucleotide
<220> FEATURE:
<221> NAME/KEY: misc_feature
<222> LOCATION: (17)..(17)
<223> OTHER INFORMATION: 2'-OMe modified nucleotide
<220> FEATURE:
<221> NAME/KEY: misc_feature
<222> LOCATION: (18)..(18)
<223> OTHER INFORMATION: 2'-OMe modified nucleotide
<220> FEATURE:
<221> NAME/KEY: misc_feature
<222> LOCATION: (19)..(19)
<223> OTHER INFORMATION: 2'-OMe modified nucleotide with a
3'-phosphorothioate linkage
<220> FEATURE:
<221> NAME/KEY: misc_feature
<222> LOCATION: (20)..(20)
<223> OTHER INFORMATION: 2'-OMe modified nucleotide with a
3'-phosphorothioate linkage
<220> FEATURE:
<221> NAME/KEY: misc_feature
<222> LOCATION: (21)..(21)
<223> OTHER INFORMATION: 2'-OMe modified nucleotide

<400> SEQUENCE: 6
caaguugagu accuccuuau u 21

THERAPEUTIC DELIVERY MOIETIES AND USES THEREOF

The present invention relates to novel compounds comprising novel delivery moieties for delivery of oligonucleotides, which are useful in the treatment of disease, suitably diseases of the liver.

Compounds comprising oligonucleotides permit targeting genes in a sequence-specific manner for personalized treatment of many different types of diseases involving gene dysregulation. Compounds comprising oligonucleotides exhibit different mechanisms of action depending on the particular type of oligonucleotides employed. For example, RNA interference (RNAi) compound including antisense oligonucleotides (ASOs) and small interfering RNAs (siRNAs) can be used to knock-down gene expression. In contrast, other oligonucleotide containing compounds may activate a gene using an oligonucleotide, such as with short activating RNA (saRNA). By delivering oligonucleotides to a desired tissue of the patient, gene expression can be downregulated, upregulated, or corrected.

Delivery of oligonucleotides using delivery moieties comprising N-acetylgalactosamine (GalNAc) to target the asialoglycoprotein receptor on liver cells is one modality for delivery to desired tissue. An exemplary compound comprising GalNAc is givosiran, an FDA approved siRNA that targets the ALAS1 gene to treat acute hepatic porphyria. Despite the existence of such commercial compounds, there remains a need to provide alternative or improved moieties for the delivery of oligonucleotides to the liver or other tissues and improved therapeutic compounds comprising a delivery moiety and one or more oligonucleotides, such as therapeutic siRNAs.

More particularly, there is a need to provide a compound comprising a delivery moiety and one or more oligonucleotides, where such compound exhibits one or more of: improved tissue exposure, suitably improved exposure in the liver; improved liver to kidney exposure ratios, improved knockdown; an improved durable response, an improved pharmacokinetic profile, fewer off target effects, improved toxicity profiles, an improved safety profile, and/or an improved synthetic process, such as but not limited to, a synthetic process with fewer steps, a process that produces fewer degradation products, a synthetic process that produces a compound with an improved safety or efficacy profile, a process that produces improved yield, or any combination thereof.

In one form, the present invention provides a delivery moiety of Formula I:

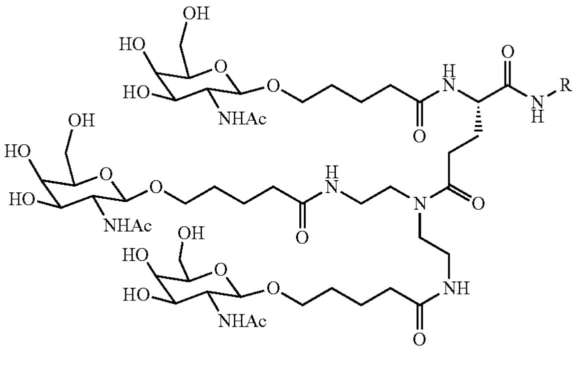

The compounds herein comprising Formula I may have modifications or additions or deletions of one or more atoms within Formula I, or the compounds may comprise additional moieties. For example, one or more alkyl chains in Formula I may be extended or shortened, or the compound comprising Formula I may further comprise one or more oligonucleotides. The compounds herein comprising Formula I are useful for, e.g. delivering one or more oligonucleotides to a cell that has a receptor for one or more N-acetylgalactosamine (GalNAc, also N-GalNAc or galnac) moieties, such as the asialoglycoprotein receptor (ASPGR) that typically binds three GalNAc moieties. Accordingly, the compounds comprising Formula I herein may be used to preferentially bind to liver cells that express ASPGR, thereby facilitating entry of the compounds into liver cells. As ASPGR is also present on adipose tissue, the compounds of Formula I thus may be used to deliver oligonucleotides to fat cells that express ASPGR.

In one embodiment is a compound comprising Formula I, wherein R comprises two hydrogen molecules attached. In another embodiment is a compound of Formula I, wherein R comprises a methyl group. In another embodiment is Formula I, wherein R comprises a protection group. In another embodiment is Formula I, wherein R is a compound comprising one or more oligonucleotides. In a suitable further embodiment, the delivery moiety comprising Formula I delivers the one or more oligonucleotides to liver tissue, by binding to the extracellular receptor ASPGR and permitting entry of the oligonucleotides into the cells that comprise the liver tissue.

The delivery moiety comprising Formula I can be used to deliver oligonucleotides for diagnostic or therapeutic purposes. The one or more oligonucleotides may comprise DNA or RNA nucleotides, or DNA or RNA nucleosides, or a any combination thereof, and may comprise one or more, or all, modified nucleotides or modified bonds.

The oligonucleotides herein are designed to target, that is, bind or anneal to certain DNA or RNA sequences in a cell to regulate gene expression. In one embodiment is a compound comprising Formula I, wherein R is an oligonucleotide for decreasing expression of a target transcript. In a further embodiment the compound comprising Formula I, wherein R is an oligonucleotide for decreasing expression of a target transcript which further decreases protein expression. In another embodiment, the decrease in expression of a target transcript or target protein is about 99, 95, 90, 85, 80, 75, 70, 65, 60, 55, or 50 percent. In a further embodiment, the decrease in expression is durable for about three weeks, about one month, about one and half months, about two months, about three months, about four months, about five months, or about six months.

One of skill in the art recognizes that one or more mismatches may be present as between the oligonucleotide and the target nucleotide sequence and still function to regulate gene expression. Accordingly, in an embodiment, the oligonucleotide has 99, 98, 97, 96, 95, 94, 93, 92, 91, 90, 89, 88, 87, 86, 85, 84, 83, 82, 81, 80, 79, 78, 77, 76, 75, 74, 73, 72, 71, or 70 percent identity with the target sequence. The oligonucleotides may also have overhangs of 1-10, 1-5, or 1-3, or 3, 2, or 1 residue(s) at either the 5' or 3' end. The 5' or 3' ends may be further modified with, for example but not limited to, an abasic residue or a phosphate group. Suitable modifications are known in the art.

One of skill in the art recognizes that 2'-modifications on the sugar residue, suitably ribose, can increase its stability and half-life. These modifications include, but are not limited to, a 2' fluoro or 2' methoxy modification in place of the 2' OH group of an unmodified sugar. One of skill in the art recognizes that changes in the backbone of an oligonucleotide can also increase its stability and half-life. These backbone modifications include a change from a phosphodiester bond to a phosphorothioate (PS) bond.

Accordingly, as used herein, oligonucleotide (or multimer or oligomer, used herein interchangeably) as used herein means a chain of at least four nucleotide or nucleoside residues, and may comprise modified or unmodified bases and/or modified or unmodified bonds. The nucleotide residues may be connected by phosphodiester bonds or modified bonds (where lacking a phosphate the residues are typically termed nucleoside as known in the art). The nucleotide or nucleoside residues may be modified at one or more atoms in the pyrimidine or purine ring, or at one or more atoms in the sugar residue, or at one or more atoms of the bond between the ring-sugar base. Modifications may also be made at the 5' or 3' end of the oligonucleotide strand and referred to as an oligonucleotide herein, unless the context makes clear otherwise.

In certain embodiments the one or more oligonucleotides comprise a small interfering RNA (siRNA), small (also called short) activating RNA (saRNA), microRNA (miRNA), short hairpin RNA (shRNA), single guide RNA (sgRNA), or antisense oligonucleotide (ASO). In a suitable embodiment the one or more oligonucleotides comprises siRNA. In another suitable embodiment the one or more oligonucleotides is an siRNA comprising a sense and antisense strand.

In some embodiments R is conjugated to Formula I via a linker. Suitable linkers are known in the art. In one embodiment, the linker comprises an alkyl chain, suitably $C_{1-10}$. In a further embodiment, the linker is shown below as Linker 1, Formula II. In another embodiment the linker comprises a piperidine. In a further suitable embodiment, the linker is shown below as Linker 2, Formula III.

Formula II

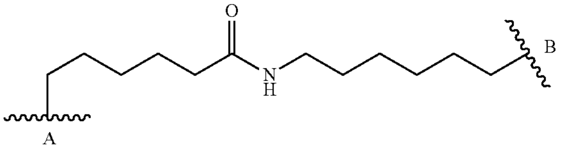

Formula III

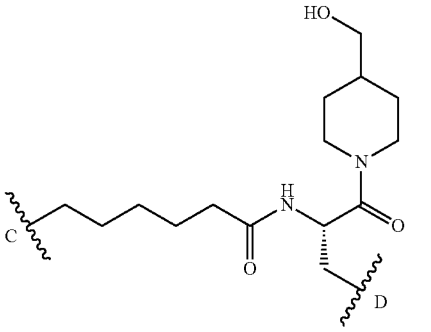

In an embodiment Linker 1 (Formula II), connection point A, or Linker 2 (Formula III), connection point C, is conjugated to Formula I. In an embodiment Linker 1, connection point A, is conjugated to Formula I and connection point B is conjugated to R. In an embodiment Linker 2, connection point C, is conjugated to Formula I and connection point D is conjugated to R. In an embodiment Linker 1, connection point A, is conjugated to Formula I and connection point B is conjugated to a phosphate group which is conjugated to R. In an embodiment Linker 2, connection point C, is conjugated to Formula I and connection point D is conjugated to a phosphate group which is conjugated to R.

One of skill in the art will recognize that the linker may be on the 5' or 3' end of an oligonucleotide, or attached to one of the internal nucleotide or nucleoside bases. One of skill in the art will also recognize that the linker maybe linked or conjugated to the 5' or 3' end of an oligonucleotide. One of skill in the art will also recognize that placement of a delivery moiety, such as the delivery moieties comprising Formula I, whether via a linker or not, on the 5' end an oligonucleotide may need to overcome potential inefficient loading of Ago2 loading, or other hindrance of the RISC complex activity. For example, for a delivery moiety comprising Formula I linked or directly conjugated to an siRNA comprising a sense and an antisense strand, placement of the delivery moiety at the 5' end of the antisense strand may create difficulties for Ago2 loading and prevent efficient knockdown. In a suitable embodiment, the one or more oligonucleotides comprise an siRNA comprising a sense and an antisense strand, and the delivery moiety comprising Formula I is present on the 3' end of the sense strand. In a further embodiment, the delivery moiety comprising Formula I is conjugated to the 3' end of the sense strand via a linker. In yet a further embodiment the linker comprises a ring structure, suitably a piperidine ring. In yet a further embodiment, the linker comprises Linker 2.

Accordingly, in one embodiment, the compounds herein comprising one or more oligonucleotides wherein a ribose of at least one nucleotide is modified with a 2' fluoro group or a 2' methoxy group. In another embodiment, the one or more oligonucleotides have one or more modified or substituted phosphodiester bonds. In a further embodiment, the one or more substituted phosphodiester bond is a PS bond. In a still further embodiment, the one or more oligonucleotides comprise at least one nucleotide is modified with a 2' fluoro or a 2' methoxy group and the backbone has one or more modified or substituted phosphodiester bonds, suitably a PS bond.

In other embodiments of the compounds disclosed herein, the one or more oligonucleotides comprise an siRNA comprising a sense strand and an antisense strand. In a further embodiment, the sense strand and the antisense strand are each between 15-40 nucleotides in length. In another embodiment, the sense strand and the antisense strand anneal, and optionally comprise one or more 5' or 3' nucleotide overhangs, one or more 5' or 3' blunt ends, or a combination of both.

In another embodiment of the compounds disclosed herein, the 5' or 3' ends are further modified. In a further embodiment, the 5' end of the antisense strand is optionally phosphorylated. In a further embodiment, the nucleotide or nucleoside at 5' end of the antisense strand comprises a 5' vinylphosphonate modification.

The compounds herein comprising Formula I and one or more oligonucleotides are useful in therapy, for diseases of the liver or involving adipose tissue. In one embodiment, is a pharmaceutical composition for administering the compounds comprising Formula I and one or more nucleotides, for use in therapy or treatment of disease. One embodiment is the compounds comprising Formula I and one or more oligonucleotides, or pharmaceutical compositions thereof, for use in therapy. A further embodiment is wherein the therapy is for diseases of the liver. An alternative embodiment is for diseases involving adipose tissue, such as involving dysregulation of genes in fat cells. Another embodiment is a method of treatment of a liver disease comprising administering a compound disclosed herein, suitably a compound comprising Formula I and one or more oligonucleotides, suitably administered in an effective amount, or a pharmaceutical composition of any of the preceding. Another embodiment is a compound disclosed herein, suitably a compound comprising Formula I and one or more oligonucleotides, or a pharmaceutical composition thereof, for use in the manufacture of a medicament, suitably for the treatment of liver disease.

In another embodiment is a compound comprising Formula IV:

Formula IV

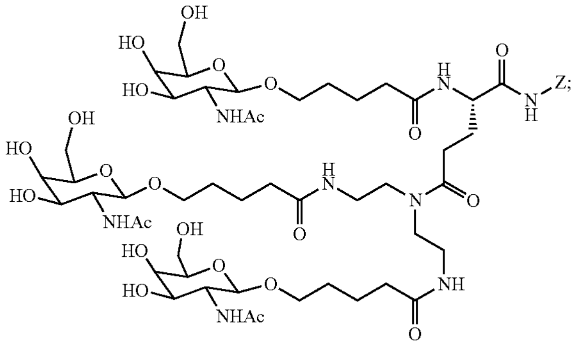

wherein Z is a solid support, resin, or bead.

The pharmaceutical compositions disclosed herein comprise one or more carriers, diluents, and excipients that are compatible with the compounds and other components of the composition or formulation and not deleterious to the patient. Examples of pharmaceutical compositions and processes for their preparation can be found in “Remington: The Science and Practice of Pharmacy”, Loyd, V., et al. Eds., 22$^{nd}$ Ed., Mack Publishing Co., 2012.

As used herein, the term “effective amount” refers to an amount that is effective in treating a disorder or disease.

As used herein, “region of complementarity” means a nucleotide sequence of a nucleic acid (e.g., a ds oligonucleotide) that is sufficiently complementary to an antiparallel nucleotide sequence to permit hybridization between the two sequences of nucleotides under appropriate hybridization conditions (e.g., in a phosphate buffer, in a cell, etc.). In some embodiments, an oligonucleotide herein includes a targeting sequence having a region of complementary to a mRNA target sequence.

A delivery moiety comprising Formula I may be made by the following nonlimiting synthetic steps and schemes.

Certain abbreviations are defined as follows: “1,2-DCE” refers to 1,2-dichloroethane; “DCM” refers to dichloromethane; “DIEA” refers to N,N-diisopropylethylamine; “DMF” refers to N,N-dimethylformamide; “DMAP” refers to 4-dimethylaminopyridine; “DMTCl” refers to 4,4'-dimethoxytrityl chloride; “DPP4” refers to dipeptidyl peptidase; “EDC” refers to 1-ethyl-3-(3-dimethylaminopropyl)carbodiimide; “EtOAc” refers to ethyl acetate; “GalNAc” refers to N-acetylgalactosamine; “HATU” refers to 1-[bis(dimethylamino)methylene]-1H-1,2,3-triazolo[4,5-b]pyridinium 3-oxid hexafluorophosphate; “HBTU” refers to O-(benzotriazol-1-yl)-N,N,N',N'-tetramethyluronium hexafluorophosphate; “HOBt” refers to 1-hydroxybenzotriazole hydrate; “HPRT” refers to hypoxanthine-guanine phosphoribosyltransferase; “IPA” refers to isopropanol and isopropyl alcohol; “LDHA” refers to lactate dehydrogenase-A; “MeCN” refers to acetonitrile; “MeOH” refers to methanol and methyl alcohol; “MWCO” refers to molecular weight cut-off; “NHS” refers to N-hydroxysuccinimide; “OD” refers to optical density; “PBS” refers to phosphate-buffered saline; “$PhSiH_3$” refers to phenylsilane; “PTS” refers to portable endotoxin testing system; “siRNA” refers to small interfering ribonucleic acid; “TEA” refers to triethylamine; “TFA” refers to trifluoroacetic acid; “THF” refers to tetrahydrofuran; “TLC” refers to thin line chromatography; and “TMP” refers to 2,2,6,6-tetramethylpiperidine Scheme 1

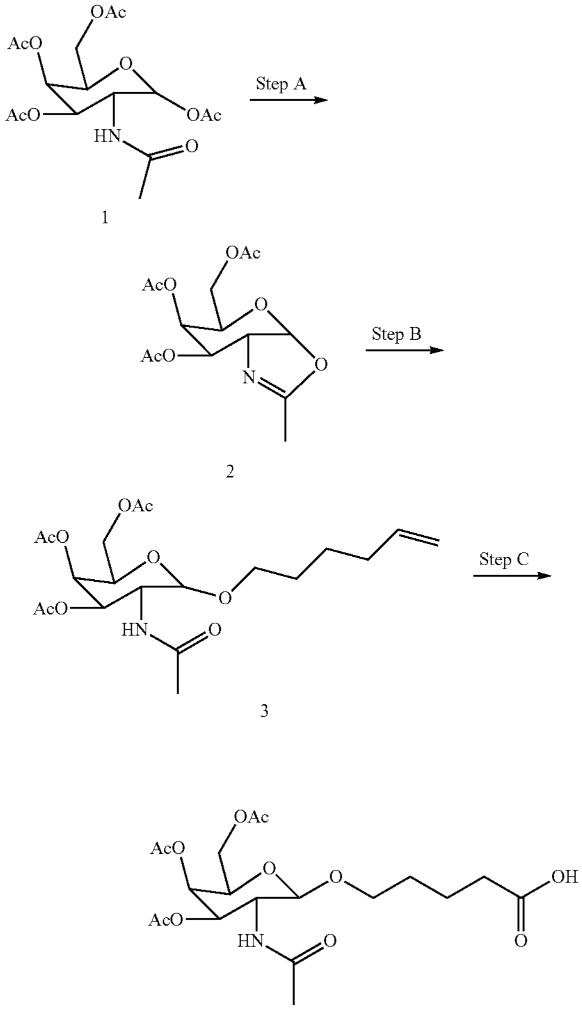

1

2

3

4

Scheme 1, step A, depicts the cyclization of compound (1) using trimethyl trifluoromethanesulfonate in a solvent such as 1,2-DCE to give compound (2). Step B shows the addition of hex-5-en-1-ol to compound (2) using trimethylsilyl trifluoromethanesulfonate in a solvent such as 1,2-DCE to give compound (3). The oxidation of compound (3) using an appropriate oxidizing agent such as sodium periodate with a catalyst such as ruthenium(II) chloride to give compound (4) is shown in step C.

Scheme 2
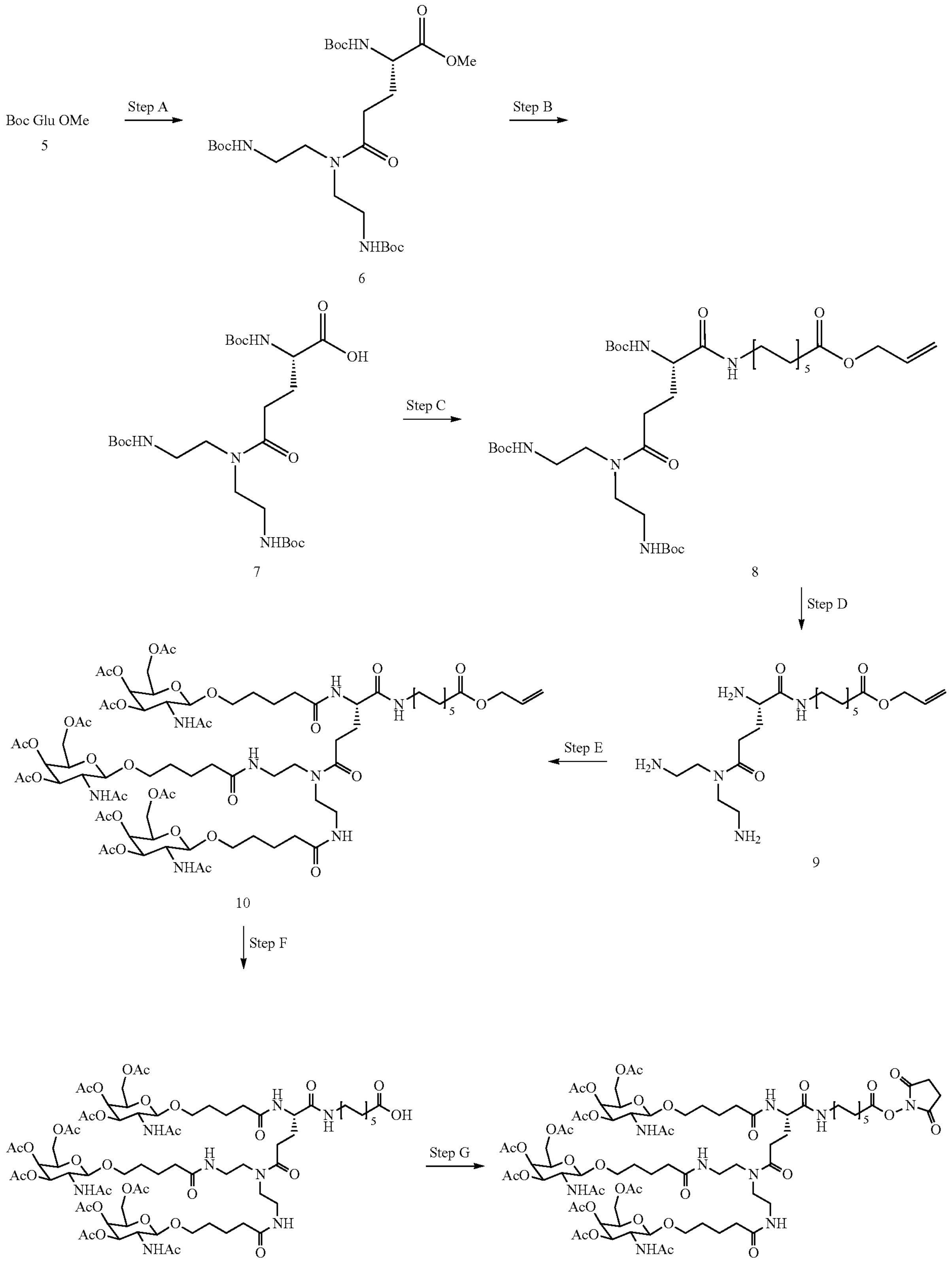
5 6 7 8 9 10 11 12

Scheme 2, step A, shows an amide coupling between compound (5) and tert-butyl N-[2-[2-(tert-butoxycarbonylamino)ethylamino]ethyl]carbamate using HBTU and HOBt with an appropriate base such as DIEA in a solvent such as DMF to give compound (6). Step B depicts a basic hydrolysis of compound (6) using a base such as aqueous NaOH in a THF and MeOH solvent system to give compound (7). Step C shows an amide coupling between compound (7) and allyl 11-aminoundecanoate hydrochloride using HATU with an appropriate base such as DIEA in a solvent such as DMF to give compound (8). Step D shows the acidic deprotection of compound (8) with TFA in a solvent such as DCM to give compound (9). The amide coupling between compound (9) and compound (4) using EDC and HOBt in a solvent such as DCM to give compound (10) is shown in step E. Step F shows the deprotection of compound (10) with tetrakis(triphenylphosphine)palladium and $PhSiH_3$ in a solvent such as DCM to give compound (11). Step F depicts the coupling of compound (11) with NHS using EDC in a solvent such as DCM to give compound (12).

Scheme 3

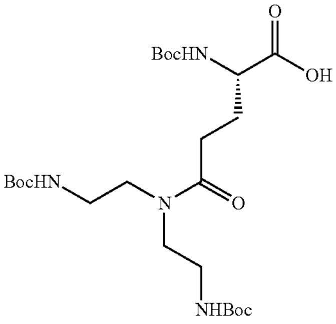

7

Step A

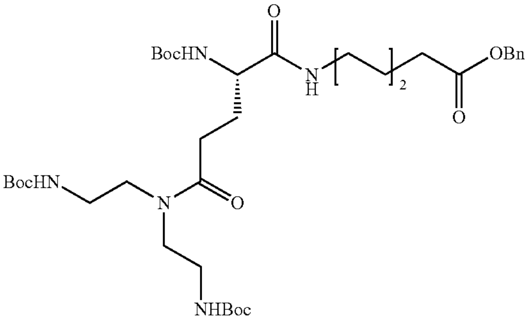

13

Step B

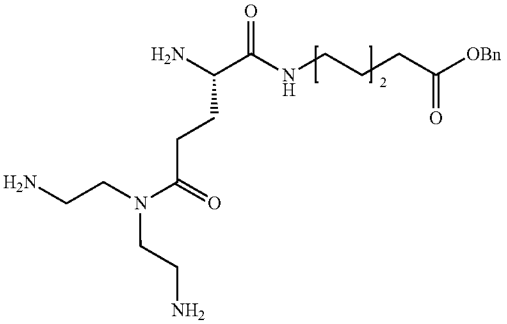

14

Step C

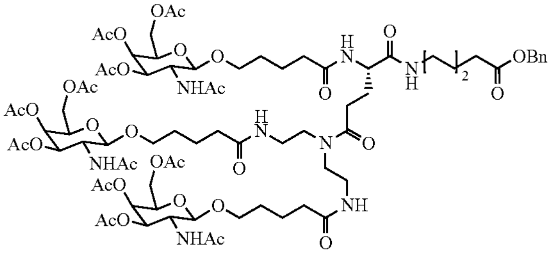

15

Step D

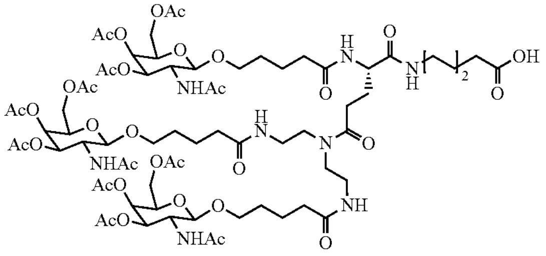

16

Step E

-continued
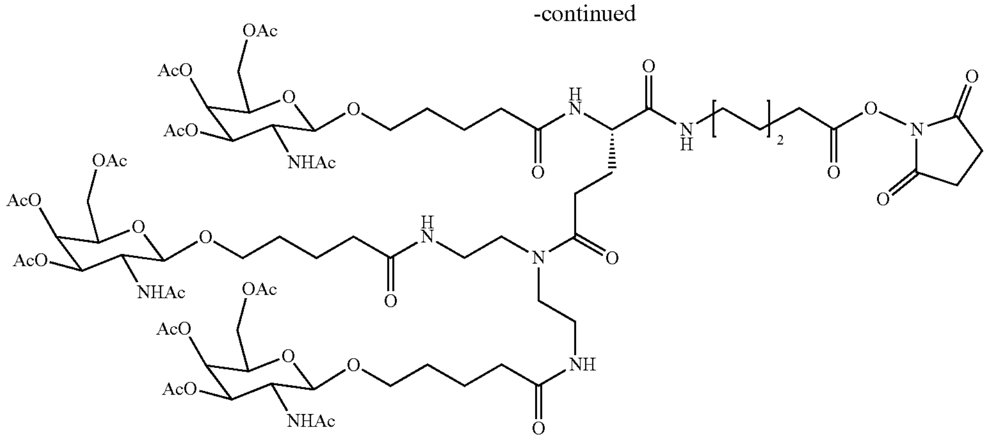
17
Scheme 3, steps A-C are essentially analogous to those of scheme 2, steps C-E beginning with compound (7) to give compounds (13), (14), and (15). Step D depicts the hydrogenation of compound (15) using palladium on carbon in a solvent such as MeOH to give compound (16). Step E is essentially analogous to the preparation of scheme 2, step G to give compound (17).
Scheme 4
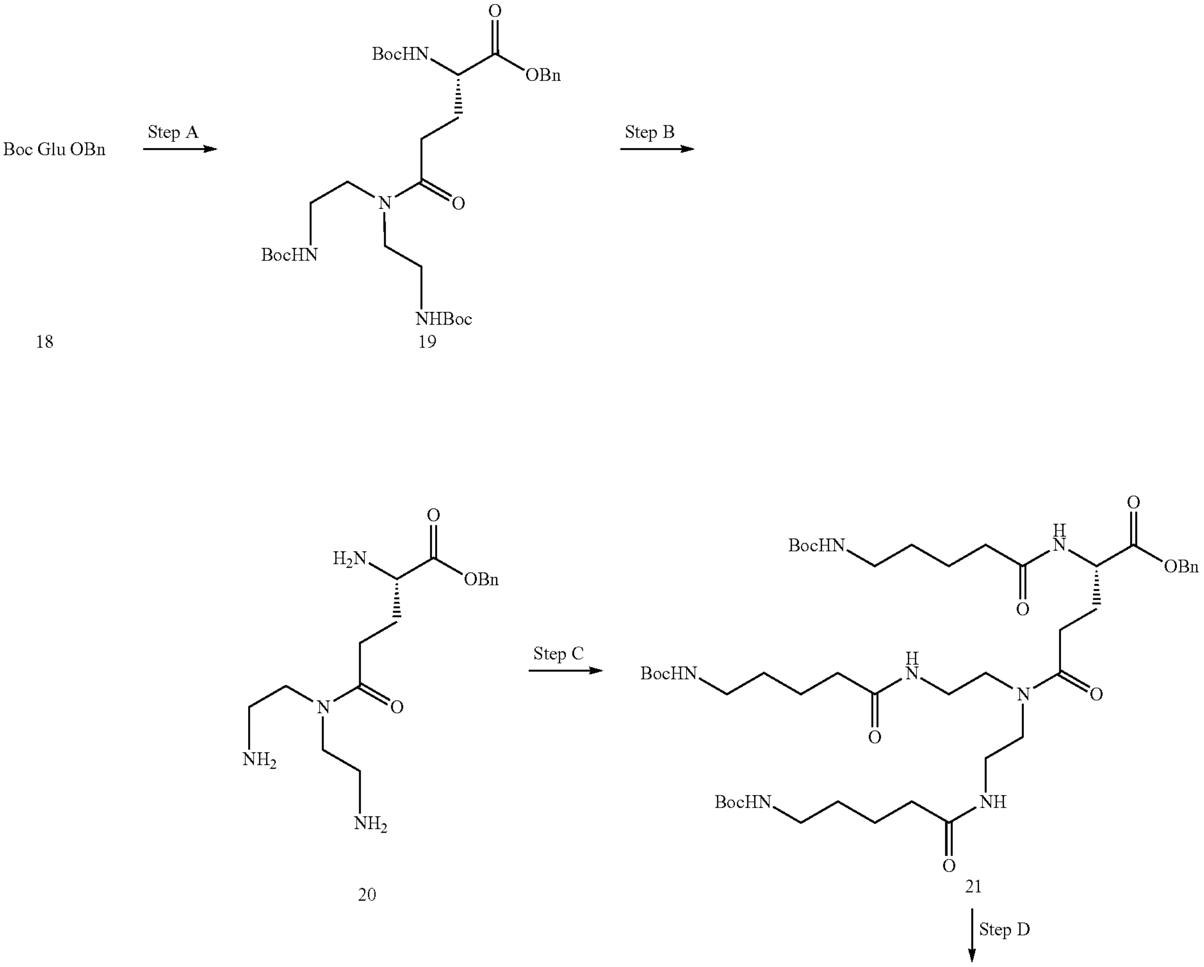
18
19
20
21

-continued
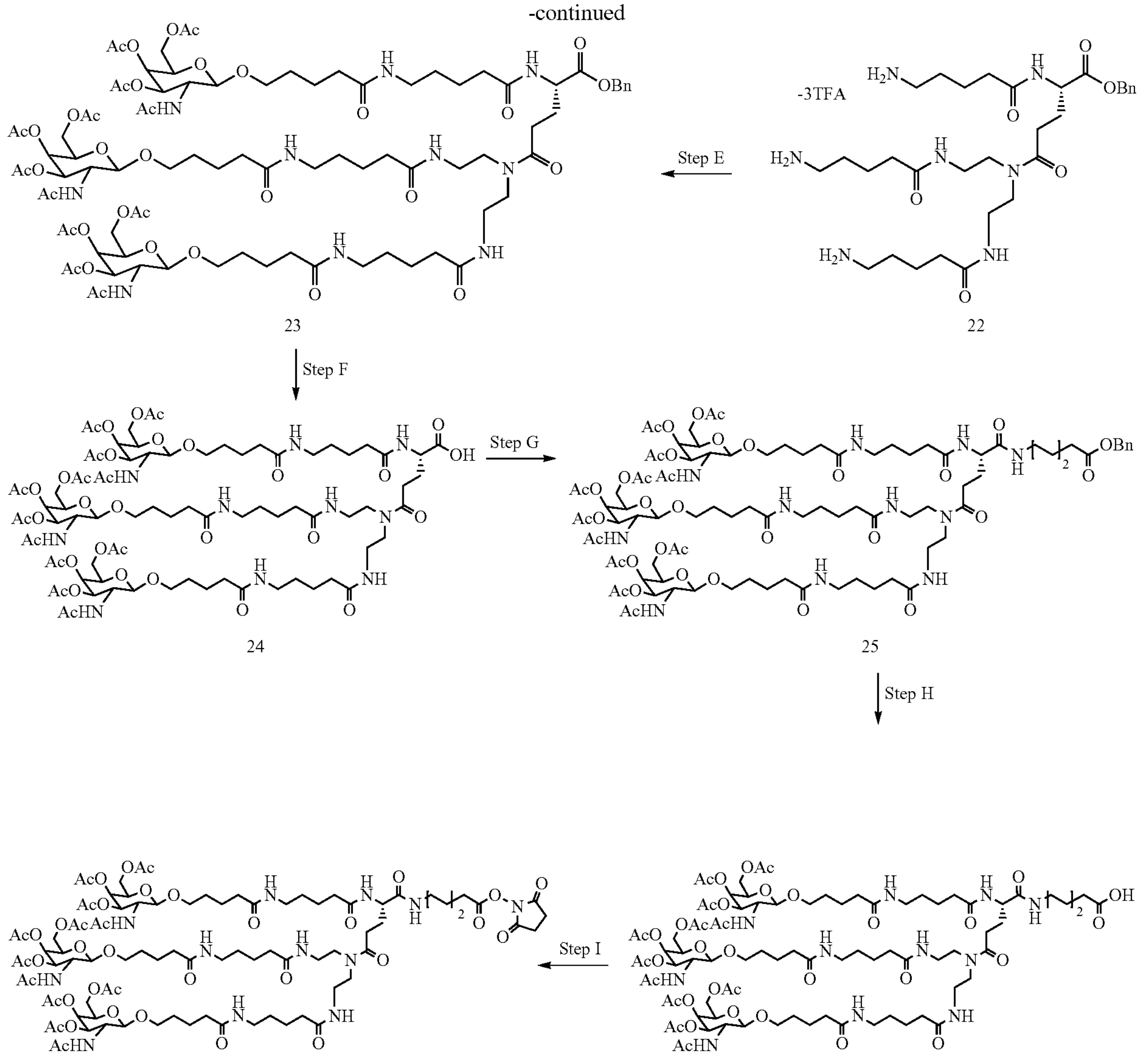
23 22 24 25 27 26
Scheme 4, steps A-I, are composed of a series of amide couplings and deprotections using methods essentially analogous to those found in schemes 2 and 3 beginning with compound (18) to give compound (27).
Scheme 5
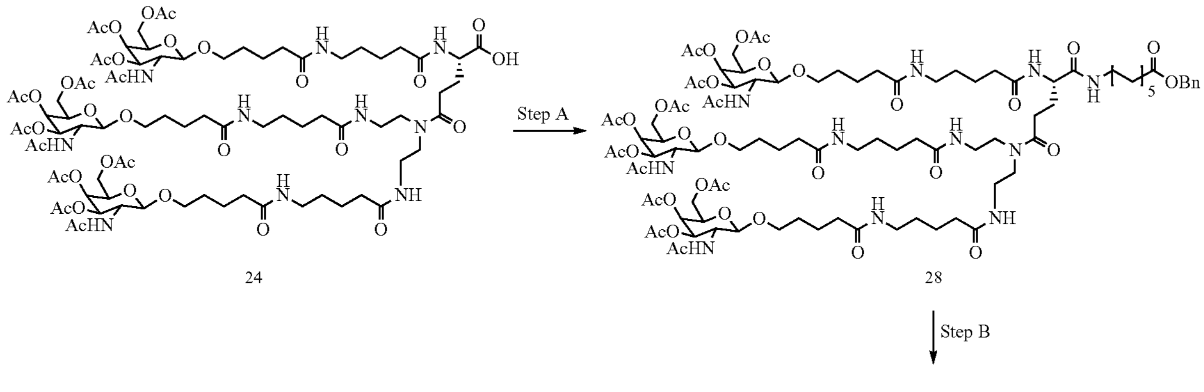
24 28

-continued

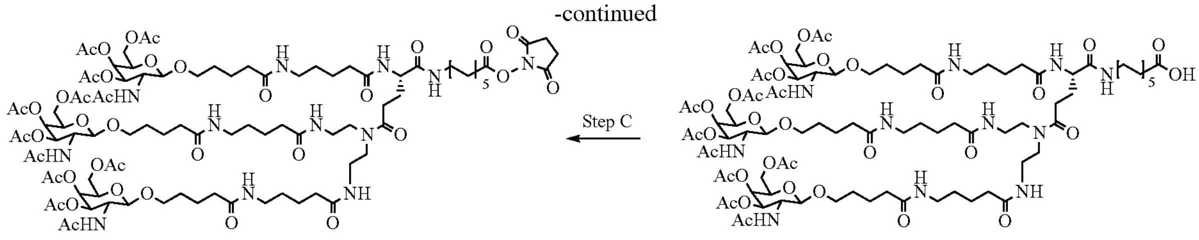

30 29

Scheme 5, steps A-C depict methods essentially analogous to those found in scheme 4, steps G-I beginning with compound (24) to give compound (30).

Scheme 6

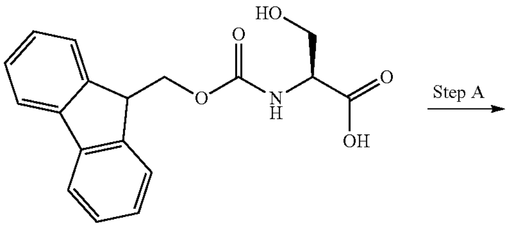

31

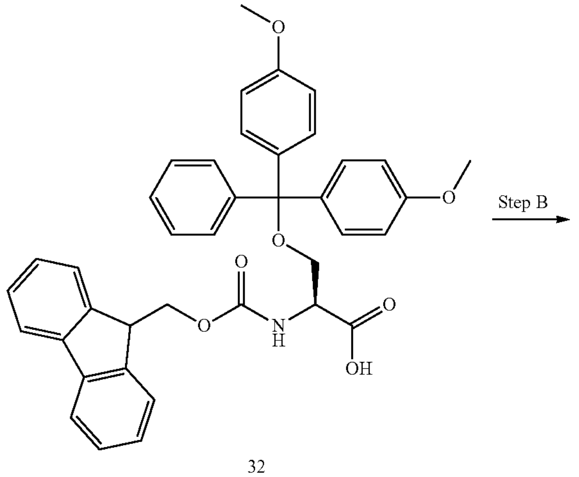

32

-continued

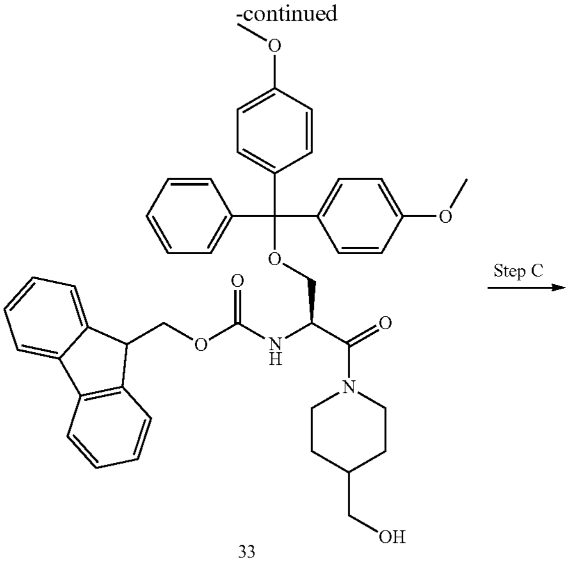

33

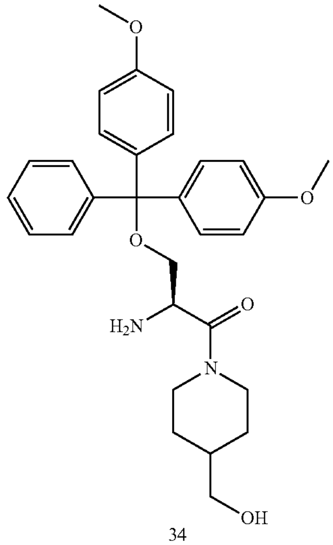

34

Scheme 6, step A depicts the protection of compound (31) using DMTCl with a suitable base such as DIEA in a solvent such as DCM to give compound (32). Step B shows an amide coupling between compound (32) and piperidin-4-yl methanol using HBTU and HOBt with TMP in a solvent such as DCM to give compound (33). The deprotection of compound (33) with 20% piperidine in DMF to give compound (34) is shown in step C.

Scheme 7
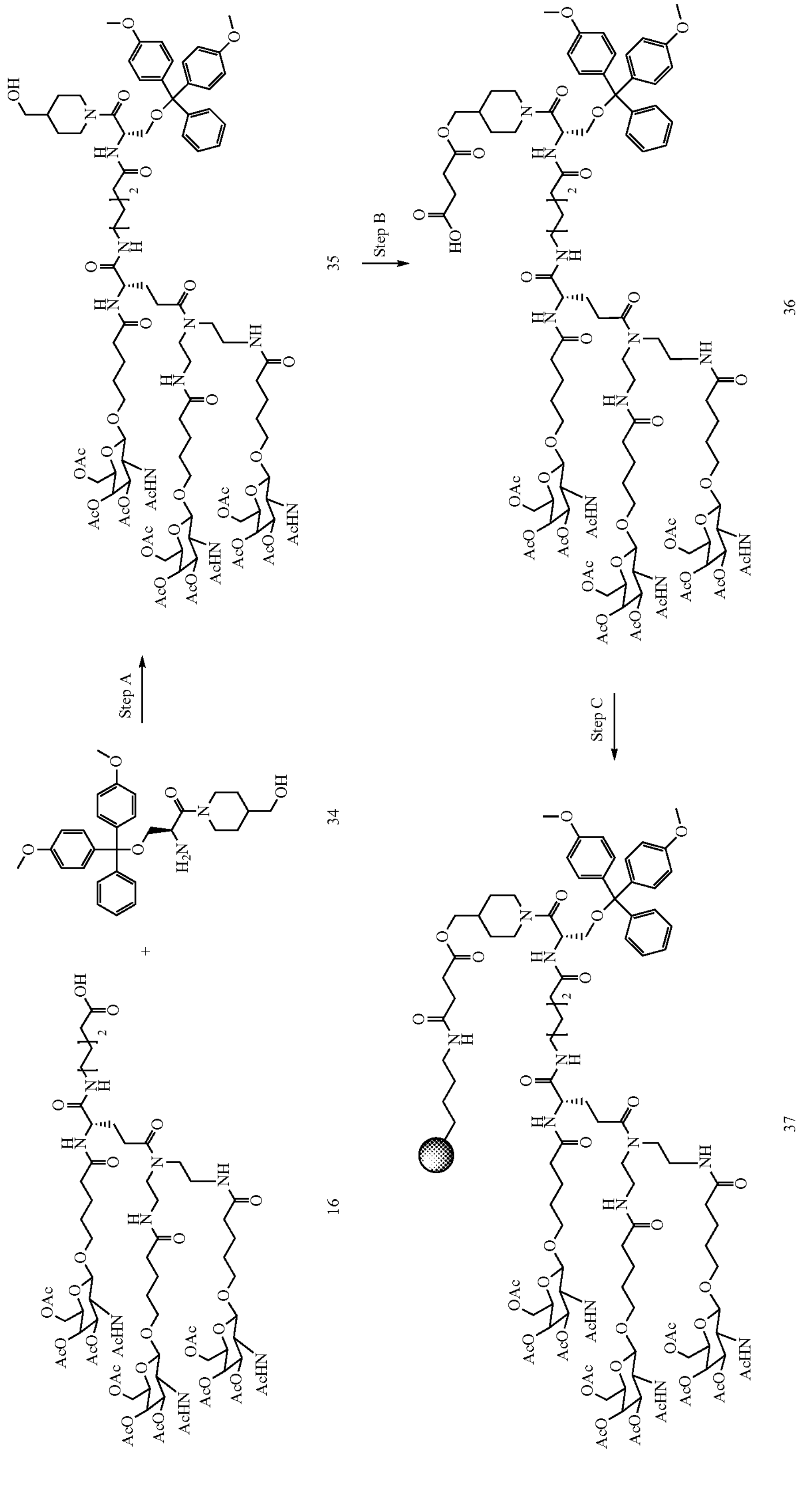
16 34 35 36 37

Scheme 7, step A is essentially analogous to scheme 2, step A to give compound (35) from the coupling of compounds (16) and (34). Step B shows the formation of compound (36) by adding succinic anhydride to compound (35) in an appropriate solvent such as DCM with a base system of TEA and DMAP. Step C depicts the loading of compound (36) onto resin with 2-(1H-benzotriazol-1-yl)-1,1,3,3-tetramethyluronium hexafluorophosphate and a base such as DIEA in a solvent system such as MeCN and DCM to give compound (37).

Preparation 1

(6,7-Diacetoxy-2-methyl-5,6,7,7a-tetrahydro-3aH-pyrano[3,2-d]oxazol-5-yl)methyl acetate

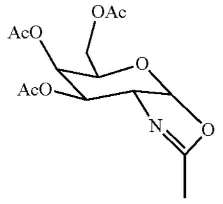 [SMILES: CC(=O)OCC1OC2OC(C)=NC2C(OC(C)=O)C1OC(C)=O]

To a solution of (5-acetamido-3,4,6-triacetoxy-tetrahydropyran-2-yl)methyl acetate (9.00 g, 23.1 mmol) in 1,2-DCE (46 mL) is added trimethylsilyl trifluoromethanesulfonate (6.5 mL, 35 mmol). The mixture is heated to 50° C. and stirred for 18 hours. After this time, the mixture is diluted with DCM (200 mL), washed with saturated $NaHCO_3$ (200 mL), and saturated aqueous sodium chloride solution (200 mL), dried over sodium sulfate, filtered, and concentrated in vacuo. The resulting residue is purified by silica gel flash chromatography eluting with 0-10% MeOH/DCM to give the title compound (6.434 g, 84%). ES/MS m/z 330 (M+H).

Preparation 2

(5-Acetamido-3,4-diacetoxy-6-hex-5-enoxy-tetrahydropyran-2-yl)methyl acetate

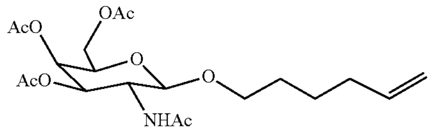 [SMILES: C=CCCCCOC1OC(COC(C)=O)C(OC(C)=O)C(OC(C)=O)C1NC(C)=O]

To a solution of (6,7-diacetoxy-2-methyl-5,6,7,7a-tetrahydro-3aH-pyrano[3,2-d]oxazol-5-yl)methyl acetate (30.43 g, 92.42 mmol) in 1,2-DCE (231 mL) is added hex-5-en-1-ol (22.2 mL, 185 mmol) followed by activated powdered 4 Å molecular sieves (15.6 g). The suspension is stirred at ambient temperature for 30 minutes and trimethylsilyl trifluoromethanesulfonate (19 mL, 101.9 mmol) is then added. The mixture is stirred at ambient temperature for 18 hours. After this time, the solution is filtered through diatomaceous earth and concentrated in vacuo. The resulting residue is purified by silica gel flash chromatography eluting with 30-100% EtOAc/hexanes to give the title compound (34.76 g, 86%). ES/MS m/z 430.4 (M+H).

Preparation 3

5-[3-Acetamido-4,5-diacetoxy-6-(acetoxymethyl)tetrahydropyran-2-yl]oxypentanoic acid

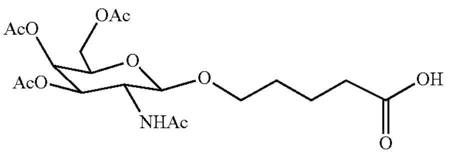 [SMILES: CC(=O)NC1C(OCCCCC(=O)O)OC(COC(C)=O)C(OC(C)=O)C1OC(C)=O]

A solution of (5-acetamido-3,4-diacetoxy-6-hex-5-enoxy-tetrahydropyran-2-yl)methyl acetate (34.76 g, 80.93 mmol) in MeCN (174 mL) and DCM (174 mL) is cooled to 0° C. A solution of sodium periodate (22.4 g, 104.7 mmol) is added and stirring is continued at 0° C. for 10 minutes. After this time, ruthenium(III) chloride (270 mg, 1.3 mmol) is added and the mixture is stirred while warming to ambient temperature. After stirring for 2 hours, additional sodium periodate (66 g, 308.4 mmol) is added and stirring is continued for 18 hours. After this time, the mixture is extracted with 3:1 $CH_3Cl$:IPA (2×500 mL), washed with saturated aqueous sodium chloride solution (1 L), dried over sodium sulfate, filtered, and concentrated in vacuo. The resulting residue is purified by silica gel flash chromatography eluting with 0-40% MeOH/DCM to give the title compound (29.75 g, 82%). ES/MS m/z 448.4 (M+H).

Preparation 4

Benzyl 6-aminohexanoate hydrochloride

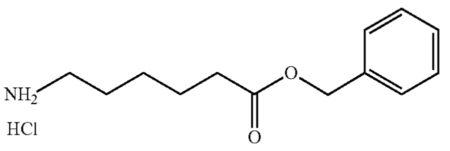 [SMILES: Cl ; NCCCCCC(=O)OCc1ccccc1]

To a suspension of 6-aminohexanoic acid (5.00 g, 38.1 mmol) in THF (38 mL) is added benzyl alcohol (47 mL, 453.7 mmol) and the mixture is cooled to 0° C. Thionyl chloride (8.6 mL, 120 mmol) is added dropwise and the mixture is stirred for 18 hours while warming to ambient temperature. After this time, ether (166 mL) is added and the reaction vessel is transferred to a freezer at −20° C. for 1 hour. After this time, the solid precipitate is collected by filtration to give the title compound (8.57 g, 81%). ES/MS m/z 222 (M+H).

Preparation 5

Benzyl 11-aminoundecanoate hydrochloride

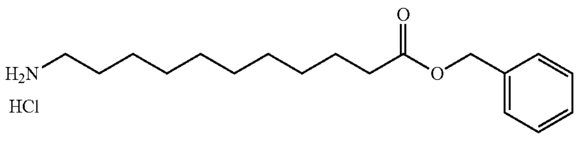 [SMILES: Cl ; NCCCCCCCCCCC(=O)OCc1ccccc1]

The title compound is prepared from 11-aminoundecanoic acid in a manner essentially analogous to the method of preparation 4. ES/MS m/z 292.2 (M+H).

Preparation 6 Allyl 11-aminoundecanoate hydrochloride

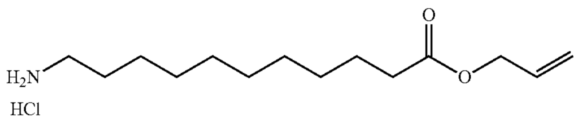 [SMILES: C=CCOC(=O)CCCCCCCCCCN ; Cl]

A vessel is charged with 11-aminoundecanoic acid (9.00 g, 44.7 mmol) in allyl alcohol (42 mL) and the mixture is cooled to 0° C. Thionyl chloride (6.5 mL, 89.4 mmol) is added and the mixture is stirred for 18 hours while warming to ambient temperature. After this time, the mixture is concentrated in vacuo and ether (200 mL) is added to the residue to obtain a white suspension. The mixture is stirred at ambient temperature for 10 minutes and the solid precipitate is collected by filtration to obtain the product (12.0 g, 97%). ES/MS m/z 242.2 (M+H).

Preparation 7

(2S)-3-[Bis(4-methoxyphenyl)-phenyl-methoxy]-2-(9H-fluoren-9ylmethoxycarbonylamino) propanoic acid

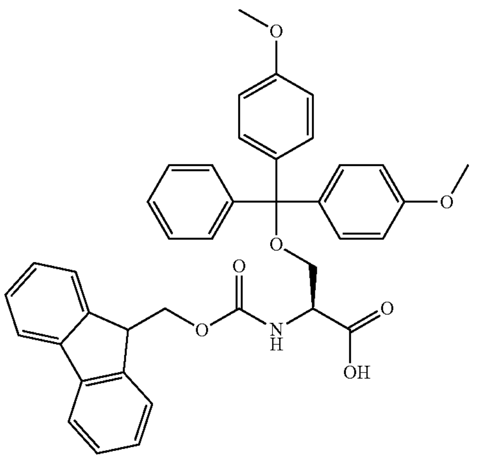 [SMILES: COc1ccc(C(OC[C@H](NC(=O)OCC2c3ccccc3-c3ccccc32)C(=O)O)(c2ccccc2)c2ccc(OC)cc2)cc1]

To a stirring solution of (2S)-2-(9H-fluoren-9-ylmethoxycarbonylamino)-3-hydroxy-propanoic acid (40 g, 0.122 mol) in dry DCM (400 mL) is added DIEA (64 mL, 0.366 mol) at 0° C. under inert atmosphere. To this, a solution of DMTCl (49.6 g, 0.146 mol) in DCM (200 mL) is added slowly. The resulting reaction mixture is brought to ambient temperature and stirred for 16 hours. After this time, the reaction mixture is diluted with water (12.5 vol) and extracted with DCM (25 vol). The organic layer is dried over anhydrous sodium sulphate, filtered, and concentrated in vacuo. The crude obtained is washed with 10% EtOAc/hexane (12.5 vol) and dried under vacuum to give the title compound as a pale brown solid (62 g, crude). This material was taken to next step without any further purification. TLC: 5% MeOH/$CH_2Cl_2$ ($R_f$: 0.5) UV, 254 nM.

Preparation 8

9H-Fluoren-9-ylmethyl N-[(1S)-1-[[bis(4-methoxyphenyl)-phenyl-methoxy]methyl]-2-[4-(hydroxymethyl)-1-piperidyl]-2-oxo-ethyl]carbamate

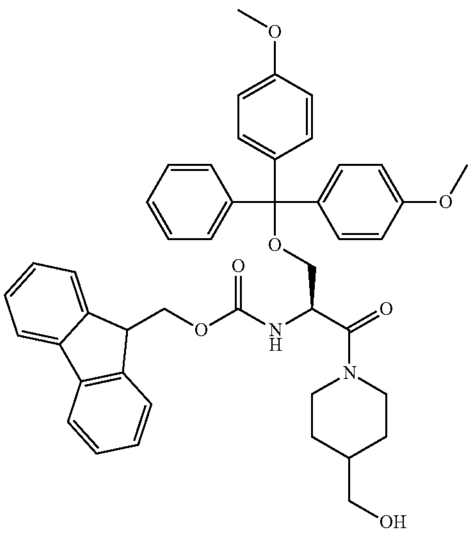 [SMILES: COc1ccc(C(OC[C@H](NC(=O)OCC2c3ccccc3-c3ccccc32)C(=O)N2CCC(CO)CC2)(c2ccccc2)c2ccc(OC)cc2)cc1]

To a stirring solution of (2S)-3-[bis(4-methoxyphenyl)-phenyl-methoxy]-2-(9H-fluoren-9ylmethoxycarbonylamino) propanoic acid (62 g, 0.103 mol) in DCM (750 mL) are added slowly HBTU (78.3 g, 0.206 mol), HOBt (27.9 g, 0.206 mol), and piperidin-4-yl methanol (15.4 g, 0.134 mol) followed by TMP (15 mL, 0.113 mol) at 0° C. under inert atmosphere. The resulting reaction mixture is brought to ambient temperature and stirred for 4 hours. After this time, the reaction mixture is diluted with water (8 vol) and extracted with DCM (15 vol). The organic layer is dried over anhydrous sodium sulphate, filtered, and concentrated in vacuo. The resulting residue is purified by silica gel flash chromatography eluting with 20-40% EtOAc/hexane and 1% MeOH/DCM to give the title compound (40 g, 52% over two steps). $^1H$ NMR (DMSO-$d_6$) δ 7.88 (br d, J=7.5 Hz, 2H), 7.79-7.59 (m, 3H), 7.45-7.12 (m, 13H), 6.92-6.76 (m, 4H), 4.79-4.44 (m, 2H), 4.32 (br d, J=11.4 Hz, 2H), 4.20 (br s, 2H), 3.71 (s, 6H), 3.21 (br s, 4H), 2.99-2.79 (m, 1H), 2.69 (br s, 2H), 1.81-1.43 (m, 3H), 1.08-0.73 (m, 2H).

Preparation 9

(2S)-2-Amino-3-[bis(4-methoxyphenyl)-phenyl-methoxy]-1-[4-(hydroxymethyl)-1-piperidyl]propan-1-one

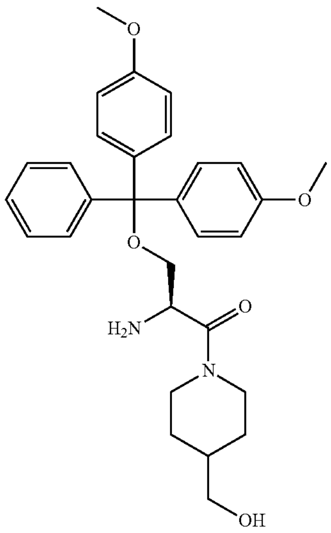 [SMILES: COc1ccc(C(OC[C@H](N)C(=O)N2CCC(CO)CC2)(c2ccccc2)c2ccc(OC)cc2)cc1]

A solution of 20% piperidine in DMF (400 mL) is added slowly to 9H-fluoren-9-ylmethyl N-[(1S)-1-[[bis(4-methoxyphenyl)-phenyl-methoxy]methyl]-2-[4-(hydroxymethyl)-1-piperidyl]-2-oxo-ethyl]carbamate (40 g, 0.055 mol) at 0° C. under inert atmosphere. The resulting reaction mixture is stirred at ambient temperature for 1 hour. After this time, the mixture is diluted with water (15 vol) and extracted with EtOAc (30 vol). The organic layer is dried over anhydrous sodium sulphate, filtered, and concentrated in vacuo. The resulting residue is purified by silica gel flash chromatography eluting with 1-8% MeOH/DCM to give the title compound as an off white solid (13 g, 47%). ES/MS m/z 1009.5 (2M+H).

Preparation 10

Methyl (2S)-5-[bis[2-(tert-butoxycarbonylamino)ethyl]amino]-2-(tert-butoxycarbonylamino)-5-oxo-pentanoate

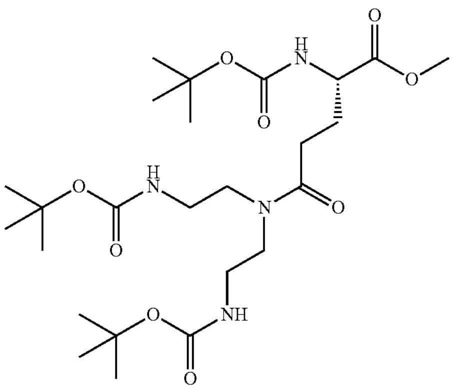 [SMILES: COC(=O)[C@H](CCC(=O)N(CCNC(=O)OC(C)(C)C)CCNC(=O)OC(C)(C)C)NC(=O)OC(C)(C)C]

To a flask containing (S)-4-((tert-butoxycarbonyl)amino)-5-methoxy-5-oxopentanoic acid (7.00 g, 26.8 mmol) and HOBt (4.16 g, 30.8 mmol) are added DMF (179 mL) and (2-(1H-benzotriazol-1-yl)-1,1,3,3-tetramethyluronium hexafluorophosphate (11.7 g, 30.9 mmol). DIEA (14 mL, 80.3 mmol) is added and the mixture is stirred at ambient temperature for 5 minutes. After this time, tert-butyl N-[2-[2-(tert-butoxycarbonylamino)ethylamino]ethyl]carbamate (8.94 g, 29.5 mmol) is added in one portion and stirring is continued at ambient temperature. After stirring for 18 hours, the mixture is diluted with EtOAc (400 mL), washed with water (2× 400 mL) and saturated aqueous sodium chloride solution (400 mL), dried over sodium sulfate, filtered, and concentrated in vacuo. The resulting residue is purified by silica gel flash chromatography eluting with 40-100% EtOAc/hexanes to give the title compound (13.01 g, 89%). ES/MS m/z 547.40 (M+H).

Preparation 11

(2S)-5-[Bis[2-(tert-butoxycarbonylamino)ethyl]amino]-2-(tert-butoxycarbonylamino)-5-oxo-pentanoic acid

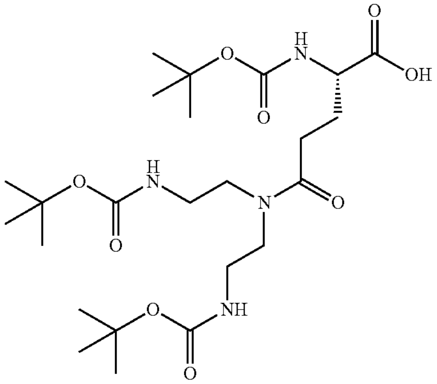 [SMILES: CC(C)(C)OC(=O)NCCN(CCNC(=O)OC(C)(C)C)C(=O)CC[C@H](NC(=O)OC(C)(C)C)C(=O)O]

A flask is charged with methyl (2S)-5-[bis[2-(tert-butoxycarbonylamino)ethyl]amino]-2-(tert-butoxycarbonylamino)-5-oxo-pentanoate (13.01 g, 23.8 mmol), THF (120 mL), and MeOH (120 mL). IN NaOH (71 mL, 71 mmol) is added and the mixture is stirred at ambient temperature. After 1 hour, the mixture is concentrated in vacuo and redissolved in water (300 mL). 5N HCl (12 mL) is added to bring the pH to 4. The mixture is extracted with DCM (3×300 mL) and the combined organic layers are washed with saturated aqueous sodium chloride solution (1 L), dried over sodium sulfate, filtered, and concentrated to give the title compound (12.41 g, 98%). ES/MS m/z 531.60 (M−H).

Preparation 12

Allyl 11-[[(2S)-5-[bis[2-(tert-butoxycarbonylamino) ethyl]amino]-2-(tert-butoxycarbonylamino)-5-oxo-pentanoyl]amino]undecanoate

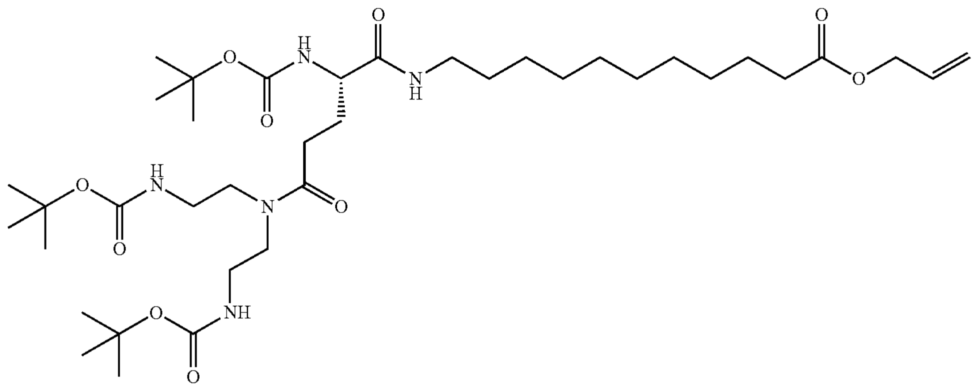 [SMILES: C=CCOC(=O)CCCCCCCCCCNC(=O)[C@H](CCC(=O)N(CCNC(=O)OC(C)(C)C)CCNC(=O)OC(C)(C)C)NC(=O)OC(C)(C)C]

To a flask containing (2S)-5-[bis[2-(tert-butoxycarbonylamino)ethyl]amino]-2-(tert-butoxycarbonylamino)-5-oxo-pentanoic acid (500 mg, 0.94 mmol) and allyl 11-aminoundecanoate hydrochloride (313 mg, 1.13 mmol) is added DMF (6.25 mL) and (1-[bis(dimethylamino)methylene]-1H-1,2,3-triazolo[4,5-b]pyridinium 3-oxide hexafluorophosphate (428 mg, 1.12 mmol). Following addition of DIEA (0.5 mL, 3 mmol) the mixture is stirred at ambient temperature for 18 hours. After this time, the mixture is diluted with EtOAc (200 mL), washed with water (3x200 mL) and saturated aqueous sodium chloride solution (200 mL), dried over sodium sulfate, filtered, and concentrated in vacuo. The resulting residue is purified by silica gel flash chromatography eluting with 40-100% EtOAc/hexanes to give the title compound (687 mg, 97%). $^1H$ NMR (DMSO-$d_6$) δ 7.78-7.64 (m, 1H), 6.98-6.7 (m, 2H), 5.96-5.84 (m, 1H), 5.31-5.25 (m, 1H), 5.23-5.17 (m, 1H), 4.56-4.50 (m, 2H), 3.88-3.67 (m, 1H), 3.30-3.19 (m, 4H), 3.11-2.91 (m, 6H), 2.35-2.12 (m, 4H), 1.88-1.65 (m, 2H), 1.58-1.47 (m, 2H), 1.46-1.30 (m, 30H), 1.30-1.18 (m, 12H).

Preparation 13

Allyl (S)-11-(2-amino-5-(bis(2-aminoethyl)amino)-5-oxopentanamido)undecanoate

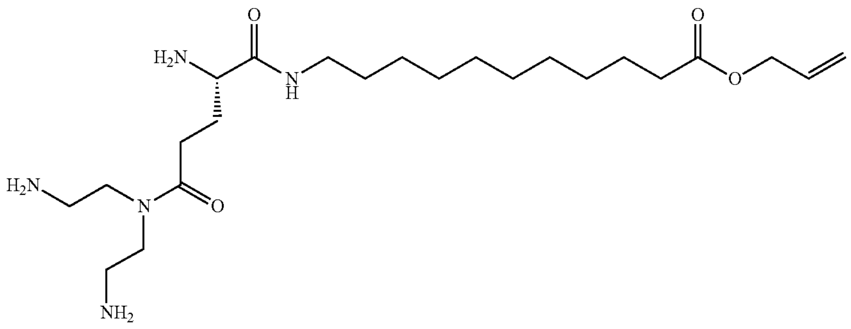 [SMILES: C=CCOC(=O)CCCCCCCCCCNC(=O)[C@@H](N)CCC(=O)N(CCN)CCN]

To a solution of allyl 11-[[(2S)-5-[bis[2-(tert-butoxycarbonylamino)ethyl]amino]-2-(tert-butoxycarbonylamino)-5-oxo-pentanoyl]amino]undecanoate (687 mg, 0.91 mmol) in DCM (15 mL) is added TFA (15 mL). The mixture is stirred at ambient temperature. After 1.5 hours, the mixture is concentrated in vacuo. The residue is taken up in MeOH and applied to an ion exchange cartridge. The cartridge is eluted with MeOH (150 mL) followed by 7N $NH_3$/MeOH (150 mL). The basic fraction is concentrated in vacuo to give the title compound (410 mg, 99%). ES/MS m/z 456.4 (M+H).

Preparation 14

Allyl 11-[[(2S)-2-[5-[3-acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl)tetrahydropyran-2-yl]oxypentanoylamino]ethyl]amino]-5-oxo-pentanoyl]amino]undecanoate

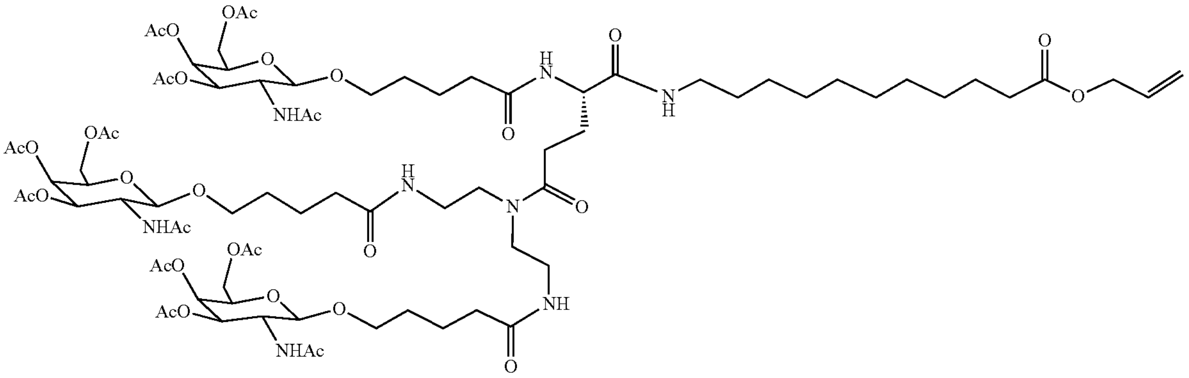

A flask is charged with 5-[3-acetamido-4,5-diacetoxy-6-(acetoxymethyl)tetrahydropyran-2-yl]oxypentanoic acid (489 mg, 1.09 mmol) and allyl (S)-11-(2-amino-5-(bis(2-aminoethyl)amino)-5-oxopentanamido)undecanoate (150 mg, 0.33 mmol). DCM (3.35 mL) is added followed by 1-hydroxybenzotriazole monohydrate (164 mg, 1.07 mmol) and 1-(3-dimethylaminopropyl)-3-ethylcarbodiimide hydrochloride (206 mg, 1.07 mmol). The mixture is stirred at ambient temperature for 18 hours. After this time, the solution is diluted with EtOAc (100 mL), washed with saturated $NaHCO_3$ (2×100 mL), saturated aqueous $NH_4Cl$ (100 mL), and saturated aqueous sodium chloride solution (100 mL). The organic layer is dried over sodium sulfate, filtered, and concentrated in vacuo. The resulting residue is purified by silica gel flash chromatography eluting with 0-10% MeOH/DCM to give the title compound (424 mg, 74%). ES/MS m/z 872.80 (M+2H)/2.

Preparation 15

11-[[(2S)-2-[5-[3-Acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl)tetrahydropyran-2-yl]oxypentanoylamino]ethyl]amino]-5-oxo-pentanoyl]amino]undecanoic acid

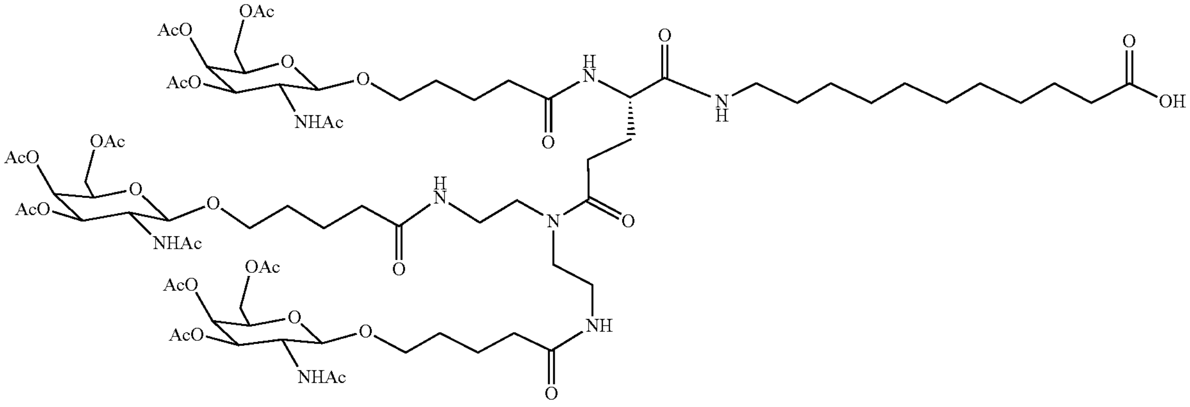

To a solution of allyl 11-[[(2S)-2-[5-[3-acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl)tetrahydropyran-2-yl]oxypentanoylamino]ethyl]amino]-5-oxo-pentanoyl]amino]undecanoate (354 mg, 0.20 mmol) in DCM (2 mL) is added tetrakis(triphenylphosphine)palladium (29 mg, 0.02 mmol) followed by $PhSiH_3$ (51 uL, 0.41 mmol). The mixture is stirred at ambient temperature for 2 hours, after which it is diluted with saturated aqueous $NaHCO_3$ (100 mL). IN NaOH (15 mL) is added to bring the pH to about 10. The aqueous solution is washed with DCM (3×100 mL) and then acidified with concentrated HCl (5 mL) and then aqueous 5N HCl (15 mL). The aqueous layer is extracted with DCM (100 mL) and the organic layer is dried over sodium sulfate, filtered, and concentrated in vacuo. The resulting residue is purified by silica gel flash chromatography eluting with 0-20% MeOH/DCM to give the title compound (151 mg, 44%). ES/MS m/z 852.60 (M+2H)/2.

Preparation 16

(2,5-Dioxopyrrolidin-1-yl) 11-[[(2S)-2-[5-[3-acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl) tetrahydropyran-2-yl]oxypentanoylamino]ethyl] amino]-5-oxo-pentanoyl]amino]undecanoate

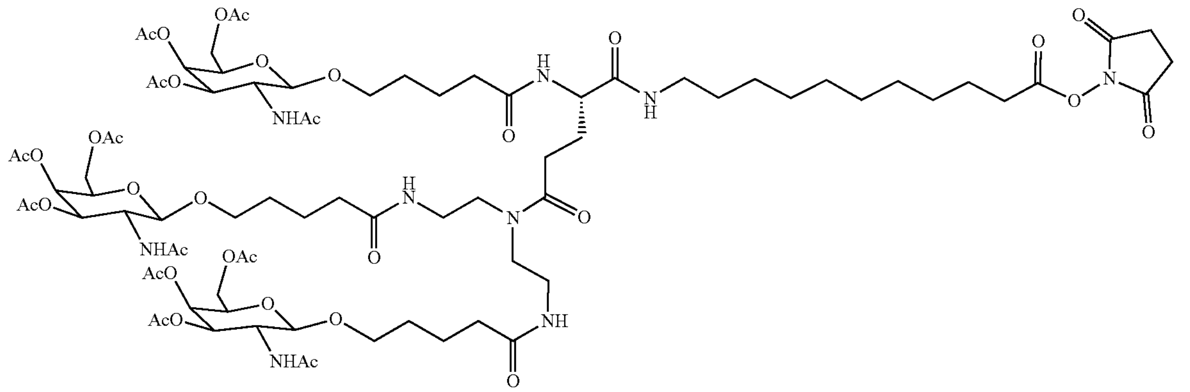 [SMILES: CC(=O)NC1C(OCCCCC(=O)NCCN(CCNC(=O)CCCCOC2OC(COC(C)=O)C(OC(C)=O)C(OC(C)=O)C2NC(C)=O)C(=O)CC[C@H](NC(=O)CCCCOC2OC(COC(C)=O)C(OC(C)=O)C(OC(C)=O)C2NC(C)=O)C(=O)NCCCCCCCCCCC(=O)ON2C(=O)CCC2=O)OC(COC(C)=O)C(OC(C)=O)C1OC(C)=O]

To a reaction vial are added 11-[[(2S)-2-[5-[3-acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl)tetrahydropyran-2-yl] oxypentanoylamino]ethyl]amino]-5-oxo-pentanoyl]amino] undecanoic acid (50 mg, 0.03 mmol), N-hydroxysuccinimide (5 mg, 0.04 mmol), and 1-(3-dimethylaminopropyl)-3-ethylcarbodiimide hydrochloride (8 mg, 0.04 mmol). DCM (0.3 mL) is added and the mixture is stirred at ambient temperature. After 18 hours, the mixture is loaded directly onto a silica gel cartridge and the crude mixture is purified by silica gel flash chromatography eluting with 0-10% MeOH/DCM to give the title compound (49 mg, 93%). ES/MS m/z 901.40 (M+2H)/2.

Preparation 17

Benzyl 6-[[(2S)-5-[bis[2-(tert-butoxycarbonylamino) ethyl]amino]-2-(tert-butoxycarbonylamino)-5-oxo-pentanoyl]amino]hexanoate

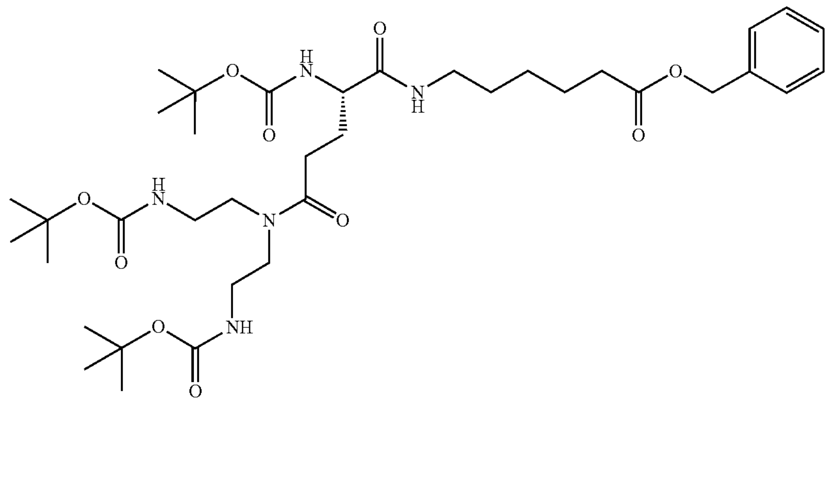 [SMILES: CC(C)(C)OC(=O)NCCN(CCNC(=O)OC(C)(C)C)C(=O)CC[C@H](NC(=O)OC(C)(C)C)C(=O)NCCCCCC(=O)OCc1ccccc1]

The title compound is prepared from (2S)-5-[bis[2-(tert-butoxycarbonylamino)ethyl]amino]-2-(tert-butoxycarbonylamino)-5-oxo-pentanoic acid and benzyl 6-amino-hexanoate hydrochloride in a manner essentially analogous to the method of preparation 10. ES/MS m/z 736.40 (M+H).

Preparation 18

Benzyl 6-[[(2S)-2-amino-5-[bis(2-aminoethyl)amino]-5-oxo-pentanoyl]amino]hexanoate tris(trifluoroacetic acid)

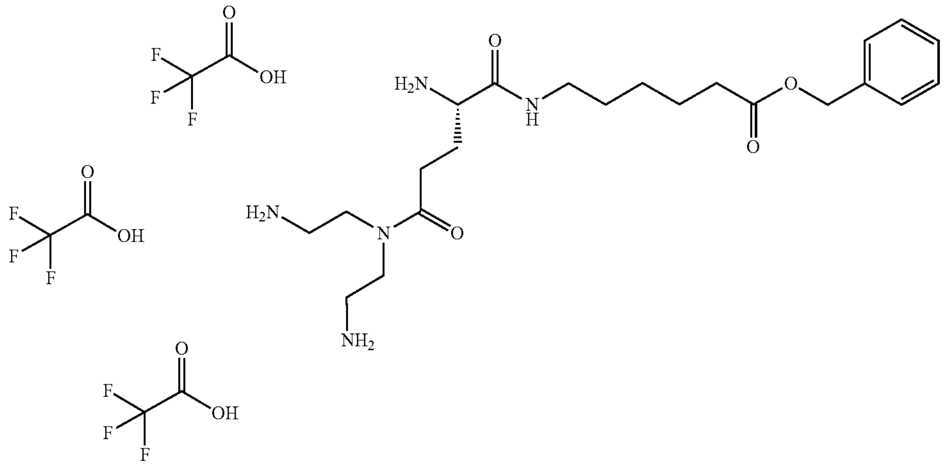 [SMILES: O=C(O)C(F)(F)F ; O=C(O)C(F)(F)F ; NCCN(CCN)C(=O)CC[C@H](N)C(=O)NCCCCCC(=O)OCc1ccccc1 ; O=C(O)C(F)(F)F]

To a solution of benzyl 6-[[(2S)-5-[bis[2-(tert-butoxycarbonylamino)ethyl]amino]-2-(tert-butoxycarbonylamino)-5-oxo-pentanoyl]amino]hexanoate (15.47 g, 21.02 mmol) in DCM (105 mL) is added TFA (16 mL, 210.2 mmol). The mixture is stirred at ambient temperature for 24 hours. After this time, additional TFA (16 mL, 210.2 mmol) is added and stirring is continued for an additional 2 hours. After this time, the mixture is concentrated in vacuo. The resulting residue is azeotroped with toluene (2×30 mL). The resulting oil is further dried in a vacuum oven at 40° C. for 4 hours to give the title compound (28.08 g, 58% purity accounting for residual toluene, 99+%). ES/MS m/z 436.40 (M+H). The compound is dissolved in 70 mL DMF to make a 0.3M solution that is used in the next step.

Preparation 19

Benzyl 6-[[(2S)-2-[5-[3-acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl)tetrahydropyran-2-yl]oxypentanoylamino]ethyl]amino]-5-oxo-pentanoyl]amino]hexanoate

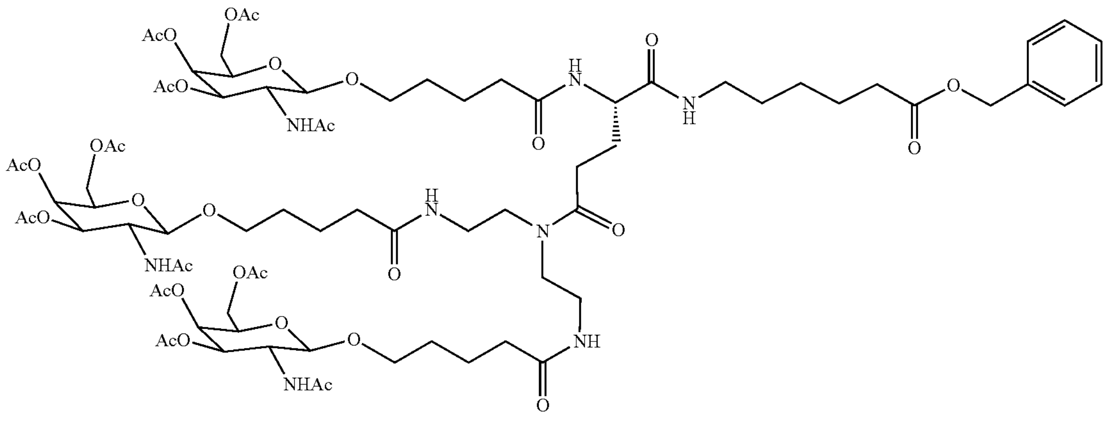 [SMILES: CC(=O)NC1C(OCCCCC(=O)NCCN(CCNC(=O)CCCCOC2OC(COC(C)=O)C(OC(C)=O)C(OC(C)=O)C2NC(C)=O)C(=O)CC[C@H](NC(=O)CCCCOC2OC(COC(C)=O)C(OC(C)=O)C(OC(C)=O)C2NC(C)=O)C(=O)NCCCCCC(=O)OCc2ccccc2)OC(COC(C)=O)C(OC(C)=O)C1OC(C)=O]

The title compound is prepared from 5-[3-acetamido-4,5-diacetoxy-6-(acetoxymethyl)tetrahydropyran-2-yl]oxy-pentanoic acid and benzyl 6-[[(2S)-2-amino-5-[bis(2-aminoethyl)amino]-5-oxo-pentanoyl]amino]hexanoate tris trifluoroacetic acid and in a manner essentially analogous to the method of preparation 10. ES/MS m/z 862 (M+2H)/2.

Preparation 20

6-[[(2S)-2-[5-[3-Acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl)tetrahydropyran-2-yl]oxypentanoylamino]ethyl]amino]-5-oxo-pentanoyl]amino]hexanoic acid

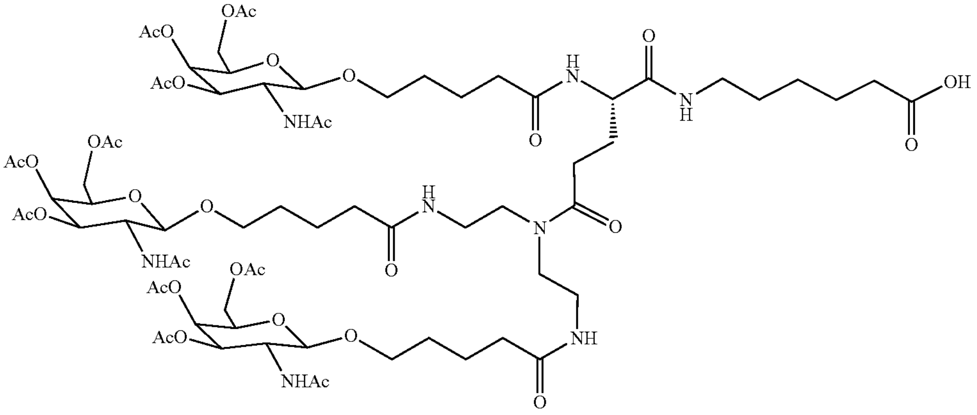 [SMILES: CC(=O)NC1C(OCCCCC(=O)NCCN(CCNC(=O)CCCCOC2OC(COC(C)=O)C(OC(C)=O)C(OC(C)=O)C2NC(C)=O)C(=O)CC[C@H](NC(=O)CCCCOC2OC(COC(C)=O)C(OC(C)=O)C(OC(C)=O)C2NC(C)=O)C(=O)NCCCCCC(=O)O)OC(COC(C)=O)C(OC(C)=O)C1OC(C)=O]

Palladium on carbon (1.90 g, 0.89 mmol, 5 mass %, 50% wet) is placed in a round-bottom flask and the vessel is evacuated and backfilled with nitrogen three times. A solution of benzyl 6-[[(2S)-2-[5-[3-acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl)tetrahydropyran-2-yl]oxypentanoylamino]ethyl]amino]-5-oxo-pentanoyl]amino]hexanoate (15.41 g, 8.94 mmol) in MeOH (178 mL) is added via syringe. The flask is evacuated and backfilled with 1 atm hydrogen and the mixture is stirred at ambient temperature under 1 atm hydrogen for 18 hours. After this time, the mixture is filtered through diatomaceous earth and the filtrate is concentrated in vacuo to give the title compound (13.85 g, 95%). ES/MS m/z 817.2 (M+2H)/2.

Preparation 21

(2,5-Dioxopyrrolidin-1-yl) 6-[[(2S)-2-[5-[3-acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl)tetrahydropyran-2-yl]oxypentanoylamino]ethyl]amino]-5-oxo-pentanoyl]amino]hexanoate

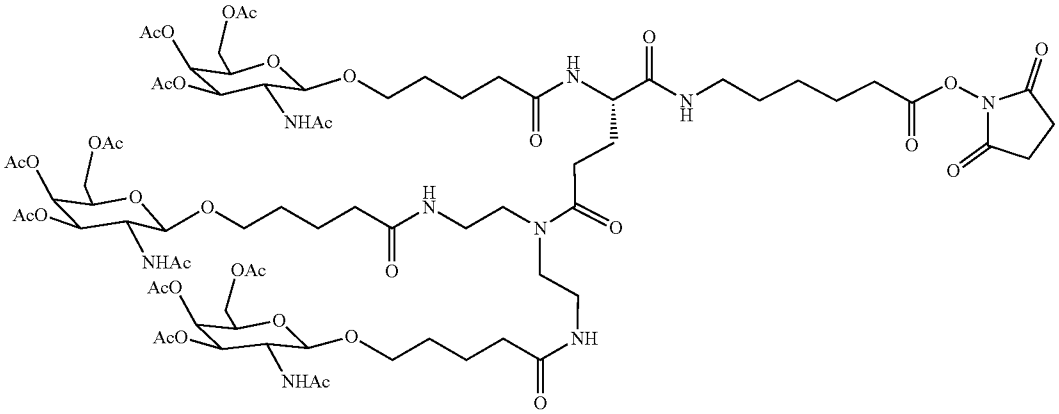 [SMILES: CC(=O)NC1C(OCCCCC(=O)NCCN(CCNC(=O)CCCCOC2OC(COC(C)=O)C(OC(C)=O)C(OC(C)=O)C2NC(C)=O)C(=O)CC[C@H](NC(=O)CCCCOC2OC(COC(C)=O)C(OC(C)=O)C(OC(C)=O)C2NC(C)=O)C(=O)NCCCCCC(=O)ON2C(=O)CCC2=O)OC(COC(C)=O)C(OC(C)=O)C1OC(C)=O]

The title compound is prepared from 6-[[(2S)-2-[5-[3-acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl)tetrahydropyran-2-yl]oxypentanoylamino]ethyl]amino]-5-oxo-pentanoyl]amino]hexanoic acid in a manner essentially analogous to the method of preparation 16. ES/MS m/z 866.20 (M+2H)/2.

Preparation 22

Benzyl (2S)-5-[bis[2-(tert-butoxycarbonylamino)ethyl]amino]-2-(tert-butoxycarbonylamino)-5-oxo-pentanoate

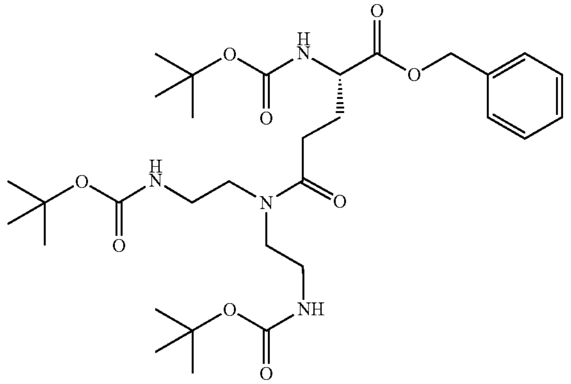 [SMILES: CC(C)(C)OC(=O)NCCN(CCNC(=O)OC(C)(C)C)C(=O)CC[C@H](NC(=O)OC(C)(C)C)C(=O)OCc1ccccc1]

The title compound is prepared from tert-butyl N-[2-[2-(tert-butoxycarbonylamino)ethylamino]ethyl]carbamate and (4S)-5-benzyloxy-4-(tert-butoxycarbonylamino)-5-oxo-pentanoic acid in a manner essentially analogous to the method of preparation 12. ES/MS m/z 623.6 (M+H).

Preparation 23

Benzyl (2S)-2-amino-5-[bis(2-aminoethyl)amino]-5-oxo-pentanoate tris(trifluoroacetic acid) salt

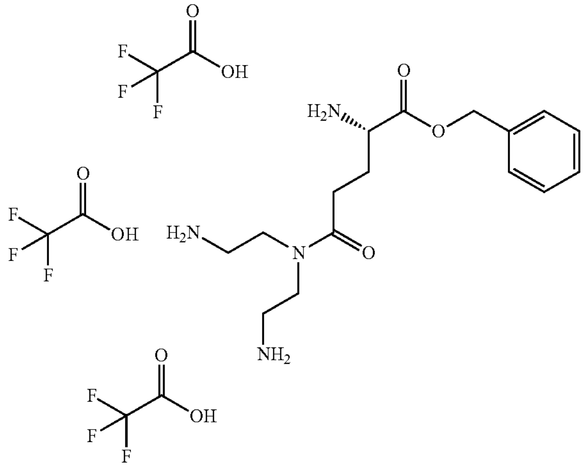 [SMILES: O=C(O)C(F)(F)F ; O=C(O)C(F)(F)F ; NCCN(CCN)C(=O)CC[C@H](N)C(=O)OCc1ccccc1 ; O=C(O)C(F)(F)F]

The title compound is prepared from benzyl (2S)-5-[bis[2-(tert-butoxycarbonylamino)ethyl]amino]-2-(tert-butoxycarbonylamino)-5-oxo-pentanoate in a manner essentially analogous to the method of preparation 18. ES/MS m/z 323.2 (M+H).

Preparation 24

Benzyl (2S)-5-[bis[2-[5-(tert-butoxycarbonylamino)pentanoylamino]ethyl]amino]-2-[5-(tert-butoxycarbonylamino)pentanoylamino]-5-oxo-pentanoate

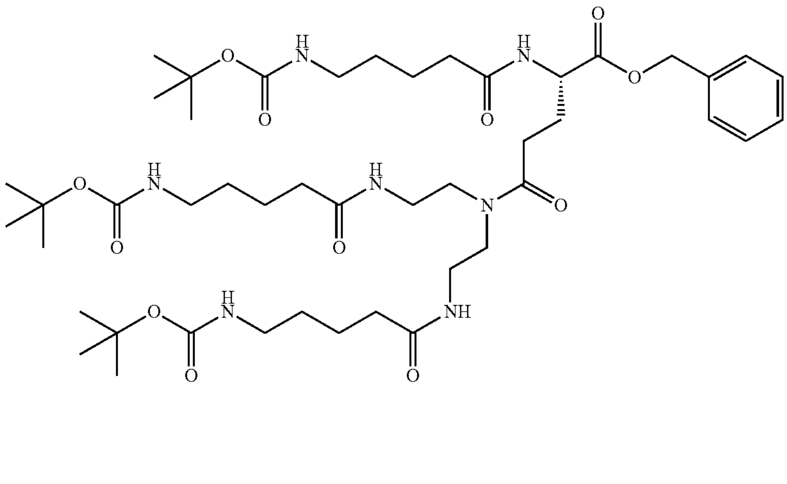 [SMILES: CC(C)(C)OC(=O)NCCCCC(=O)NCCN(CCNC(=O)CCCCNC(=O)OC(C)(C)C)C(=O)CC[C@H](NC(=O)CCCCNC(=O)OC(C)(C)C)C(=O)OCc1ccccc1]

The title compound is prepared from 5-(tert-butoxycarbonylamino)pentanoic acid and benzyl (2S)-2-amino-5-[bis(2-aminoethyl)amino]-5-oxo-pentanoate tris(trifluoroacetic acid) salt in a manner essentially analogous to the method of preparation 10. ES/MS m/z 920.6 (M+H).

Preparation 25

Benzyl (2S)-2-(5-aminopentanoylamino)-5-[bis[2-(5-aminopentanoylamino)ethyl]amino]-5-oxo-pentanoate tris(trifluoroacetic acid) salt

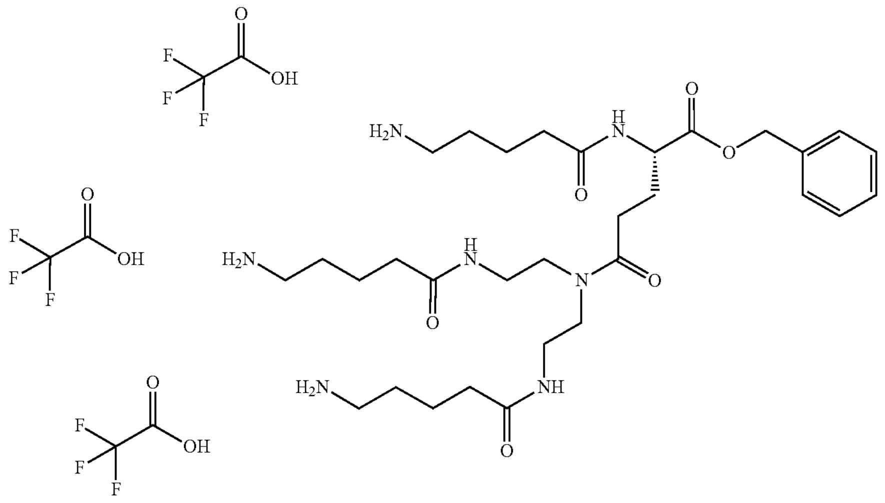 [SMILES: O=C(O)C(F)(F)F ; O=C(O)C(F)(F)F ; O=C(O)C(F)(F)F ; NCCCCC(=O)NCCN(CCNC(=O)CCCCN)C(=O)CC[C@H](NC(=O)CCCCN)C(=O)OCc1ccccc1]

The title compound is prepared from benzyl (2S)-5-[bis[2-[5-(tert-butoxycarbonylamino)pentanoylamino]ethyl]amino]-2-[5-(tert-butoxycarbonylamino)pentanoylamino]-5-oxo-pentanoate in a manner essentially analogous to the method of preparation 18. ES/MS m/z 620.4 (M+H).

Preparation 26

Benzyl (2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoate

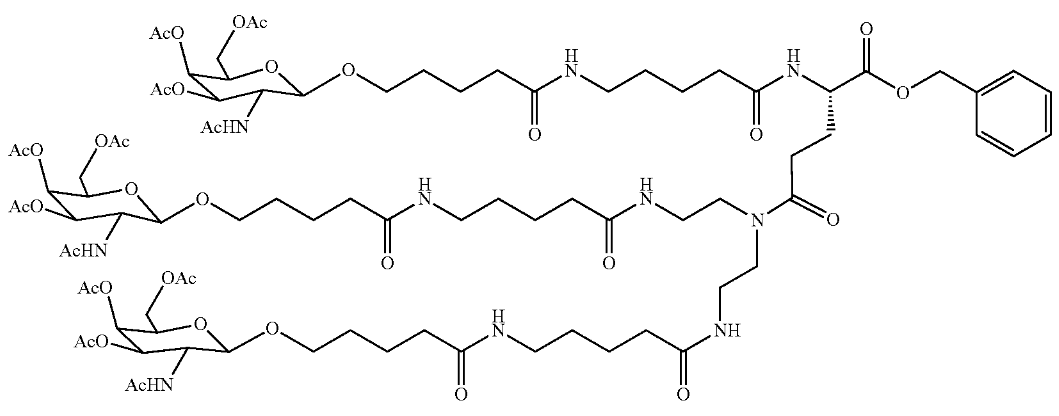 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)OCc2ccccc2)OC(COC(C)=O)C(OC(C)=O)C1OC(C)=O]

The title compound is prepared from 5-[3-acetamido-4,5-diacetoxy-6-(acetoxymethyl)tetrahydropyran-2-yl]oxy-pentanoic acid and benzyl (2S)-2-(5-aminopentanoylamino)-5-[bis[2-(5-aminopentanoylamino)ethyl]amino]-5-oxo-pentanoate tris(trifluoroacetic acid) salt and in a manner essentially analogous to the method of preparation 10. ES/MS m/z 954.80 (M+2H)/2.

Preparation 27

(2S)-2-[5-[5-[3-Acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoic acid

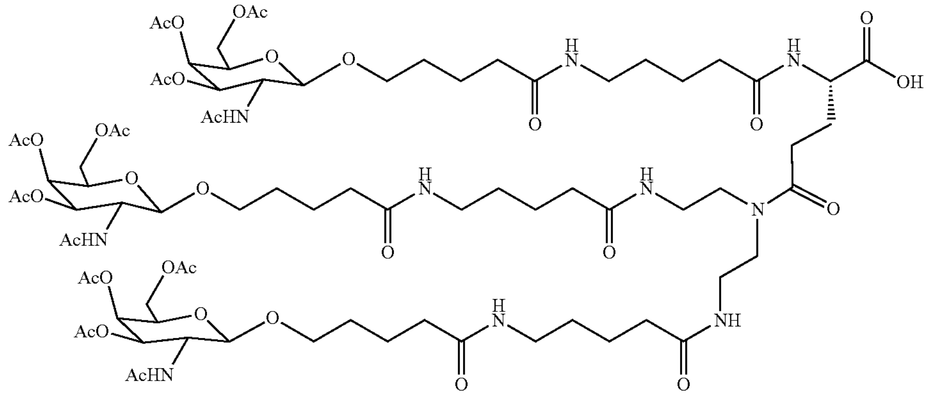 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)O)OC(COC(C)=O)C(OC(C)=O)C1OC(C)=O]

A round-bottom flask is charged with palladium on carbon (467 mg, 0.22 mmol, 5 mass %, 50% wet) and the flask is evacuated and backfilled with nitrogen three times. A solution of benzyl (2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoate (4.19 g, 2.20 mmol) in MeOH (44 mL) is added via syringe followed by three drops of acetic acid. The flask is evacuated and backfilled with 1 atm hydrogen and the mixture is stirred at ambient temperature under 1 atm hydrogen. After 2 hours, the mixture is filtered through diatomaceous earth and the filtrate is concentrated in vacuo to give the title compound (3.99 g, 99+%). ES/MS m/z 909.6 (M+2H)/2.

Preparation 28

Benzyl 6-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]hexanoate

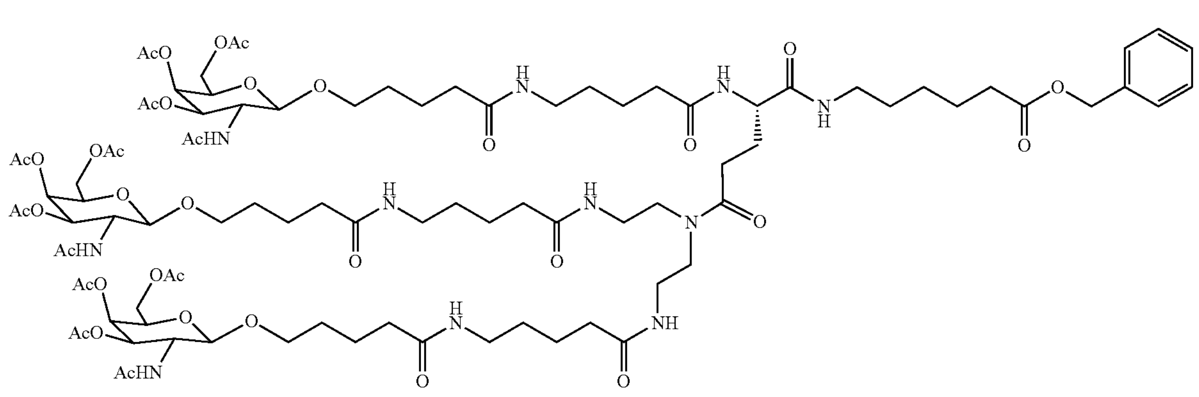 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)NCCCCCC(=O)OCc2ccccc2)OC(COC(C)=O)C(OC(C)=O)C1OC(C)=O]

The title compound is prepared from (2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoic acid and benzyl 6-aminohexanoate hydrochloride and in a manner essentially analogous to the method of preparation 10. ES/MS m/z 1011.6 (M+2H)/2.

Preparation 29

6-[[(2S)-2-[5-[5-[3-Acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]hexanoic acid

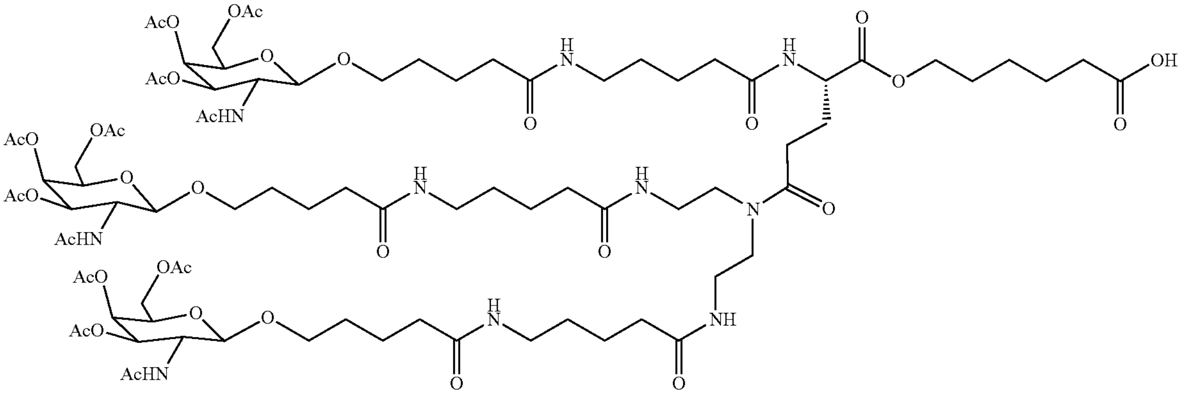 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)OCCCCCC(=O)O)OC(COC(C)=O)C(OC(C)=O)C1OC(C)=O]

A round-bottom flask is charged with palladium on carbon (24 mg, 0.01 mmol, 5% by mass, 50% wet) and the flask is evacuated and backfilled with nitrogen. A solution of benzyl 6-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]hexanoate (222 mg, 0.11 mmol) in MeOH (2.2 mL) is added via syringe followed by three drops of acetic acid. The flask is evacuated and backfilled with 1 atm hydrogen and the mixture is stirred under 1 atm hydrogen at ambient temperature. After 5 hours, the flask is purged with nitrogen and the mixture is filtered through diatomaceous earth. The filtrate is concentrated in vacuo to give the title compound (180 mg, 85%). ES/MS m/z 966.2 (M+2H)/2.

Preparation 30

(2,5-Dioxopyrrolidin-1-yl) 6-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]hexanoate

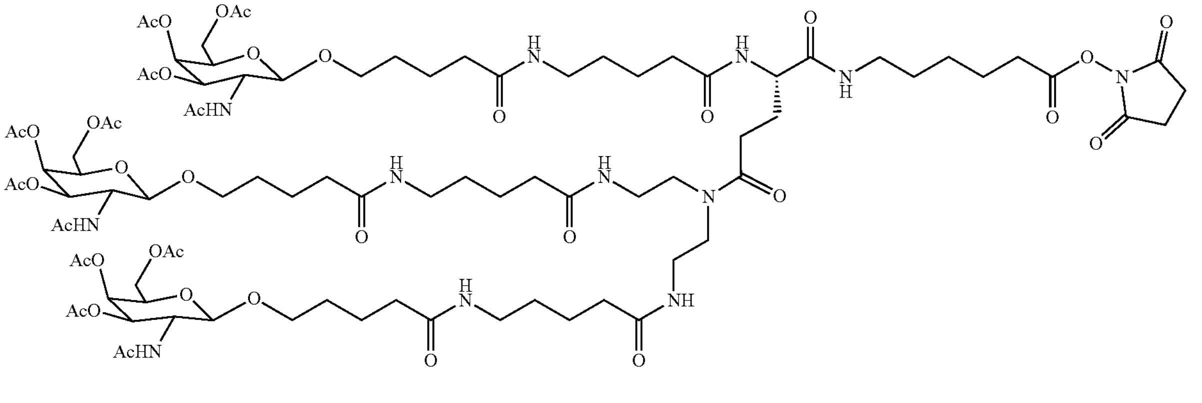 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)NCCCCCC(=O)ON2C(=O)CCC2=O)OC(COC(C)=O)C(OC(C)=O)C1OC(C)=O]

The title compound is prepared from 6-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl) tetrahydropyran-2-yl]oxypentanoylamino]pentanoylamino] ethyl]amino]-5-oxo-pentanoyl]amino]hexanoic acid in a manner essentially analogous to the method of preparation 16. ES/MS m/z 1014.6 (M+2H)/2.

Preparation 31

Benzyl 11-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl) tetrahydropyran-2-yl]oxypentanoylamino] pentanoylamino]ethyl]amino]-5-oxo-pentanoyl] amino]undecanoate

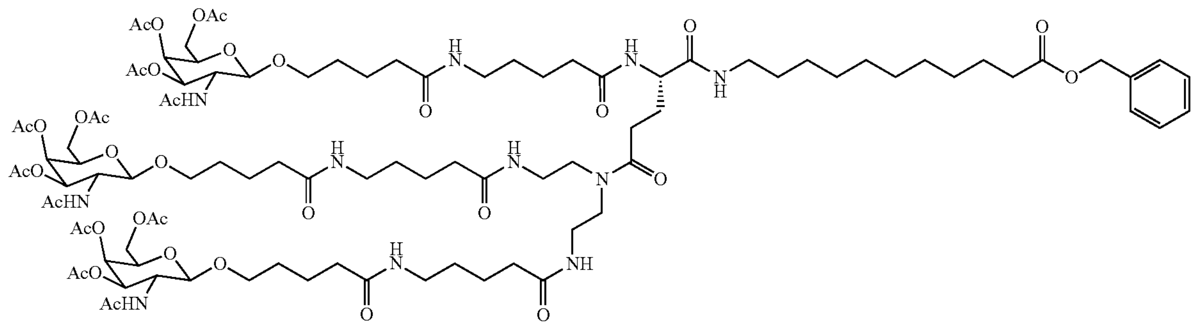 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)NCCCCCCCCCCC(=O)OCc2ccccc2)OC(COC(C)=O)C(OC(C)=O)C1OC(C)=O]

The title compound is prepared from (2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl) tetrahydropyran-2-yl]oxypentanoylamino]pentanoylamino] ethyl]amino]-5-oxo-pentanoic acid and benzyl 11-aminoudecanoate hydrochloride in a manner essentially analogous to the method of preparation 10. ES/MS m/z 1046.6 (M+2H)/2.

Preparation 32

11-[[(2S)-2-[5-[5-[3-Acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl) tetrahydropyran-2-yl]oxypentanoylamino] pentanoylamino]ethyl]amino]-5-oxo-pentanoyl] amino]undecanoic acid

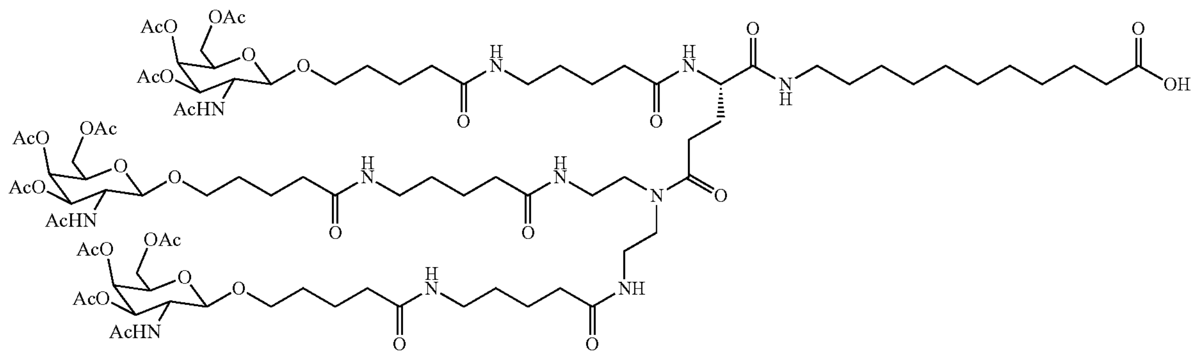 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)NCCCCCCCCCCC(=O)O)OC(COC(C)=O)C(OC(C)=O)C1OC(C)=O]

To a round-bottom flask is added palladium on carbon (35 mg, 0.02 mmol, 5 mass %, 50% wet) and the flask is evacuated and backfilled with nitrogen three times. A solution of benzyl 11-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]undecanoate (285 mg, 80% purity, 0.11 mmol) is added via syringe. The vessel is evacuated and backfilled with 1 atm hydrogen and the mixture is then stirred at ambient temperature under 1 atm hydrogen. After stirring for 3 hours, the flask is purged with nitrogen and the mixture is filtered through diatomaceous earth. The filtrate is concentrated to give the title compound (213 mg, 79% purity, 77%). ES/MS m/z 1001.20 (M+2H)/2.

Preparation 33

(2,5-Dioxopyrrolidin-1-yl) 11-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]undecanoate

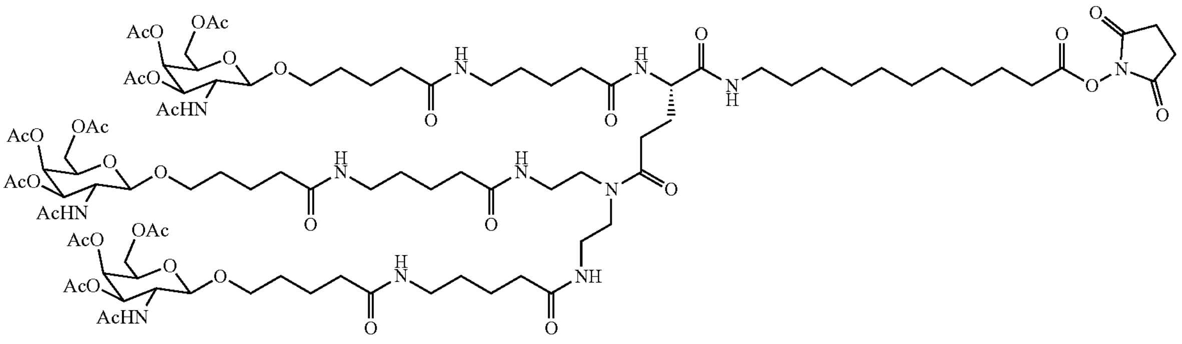 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)NCCCCCCCCCCC(=O)ON2C(=O)CCC2=O)OC(COC(C)=O)C(OC(C)=O)C1OC(C)=O]

The title compound is prepared from 11-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]undecanoic acid in a manner essentially analogous to the method of preparation 16. ES/MS m/z 1050 (M+2H)/2

Preparation 34

[5-Acetamido-6-[5-[2-[[(4S)-4-[5-[3-acetamido-4,5-diacetoxy-6-(acetoxymethyl)tetrahydropyran-2-yl]oxypentanoylamino]-5-[[6-[[(1S)-1-[[bis(4-methoxy-phenyl)-phenyl-methoxy]methyl]-2-[4-(hydroxymethyl)-1-piperidyl]-2-oxo-ethyl]amino]-6-oxo-hexyl]amino]-5-oxo-pentanoyl]-[2-[5-[3-acetamido-4,5-diacetoxy-6-(acetoxymethyl)tetrahydropyran-2-yl]oxypentanoylamino]ethyl]amino]ethylamino]-5-oxo-pentoxy]-3,4-diacetoxy-tetrahydropyran-2-yl]methyl acetate

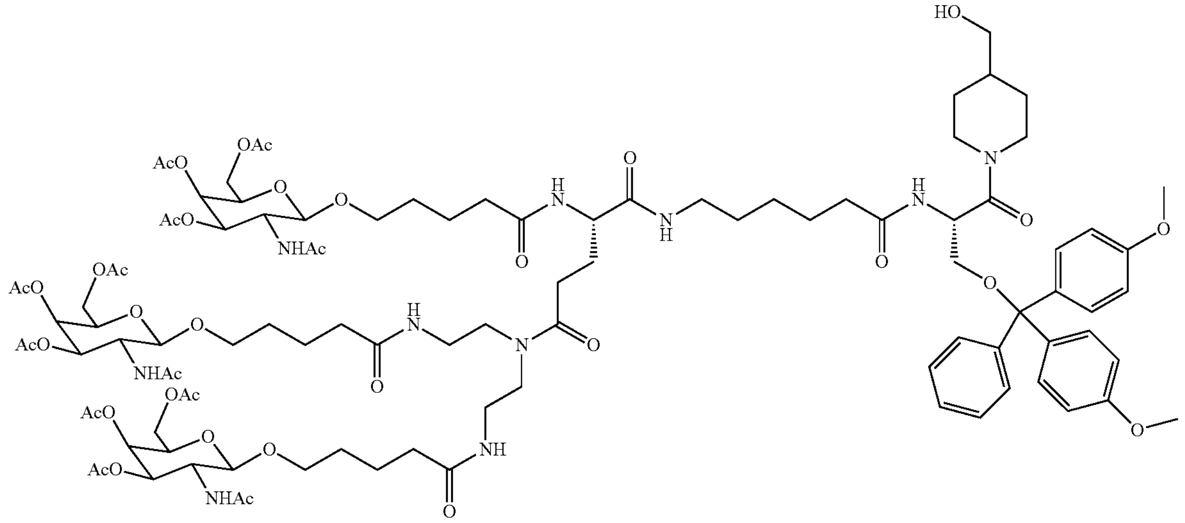 [SMILES: COc1ccc(C(OC[C@H](NC(=O)CCCCCNC(=O)[C@H](CCC(=O)N(CCNC(=O)CCCCOC2OC(COC(C)=O)C(OC(C)=O)C(OC(C)=O)C2NC(C)=O)CCNC(=O)CCCCOC2OC(COC(C)=O)C(OC(C)=O)C(OC(C)=O)C2NC(C)=O)NC(=O)CCCCOC2OC(COC(C)=O)C(OC(C)=O)C(OC(C)=O)C2NC(C)=O)C(=O)N2CCC(CO)CC2)(c2ccccc2)c2ccc(OC)cc2)cc1]

The title compound is prepared from 6-[[(2S)-2-[5-[3-acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl)tetrahydropyran-2-yl]oxypentanoylamino]ethyl]amino]-5-oxo-pentanoyl]amino]hexanoic acid and (2S)-2-amino-3-[bis(4-methoxyphenyl)-phenyl-methoxy]-1-[4-(hydroxymethyl)-1-piperidyl]propan-1-one in a manner essentially analogous to the method of preparation 10. ES/MS m/z 1059.2 (M−2H)/2.

Preparation 35

4-[[1-[(2S)-2-[6-[[(2S)-2-[5-[3-Acetamido-4,5-diacetoxy-6-(acetoxymethyl)tetrahydropyran-2-yl]oxypentanoylamino]-5-[bis[2-[5-[3-acetamido-4,5-diacetoxy-6-(acetoxymethyl)tetrahydropyran-2-yl]oxypentanoylamino]ethyl]amino]-5-oxo-pentanoyl]amino]hexanoylamino]-3-[bis(4-methoxyphenyl)-phenyl-methoxy]propanoyl]-4-piperidyl]methoxy]-4-oxo-butanoic acid

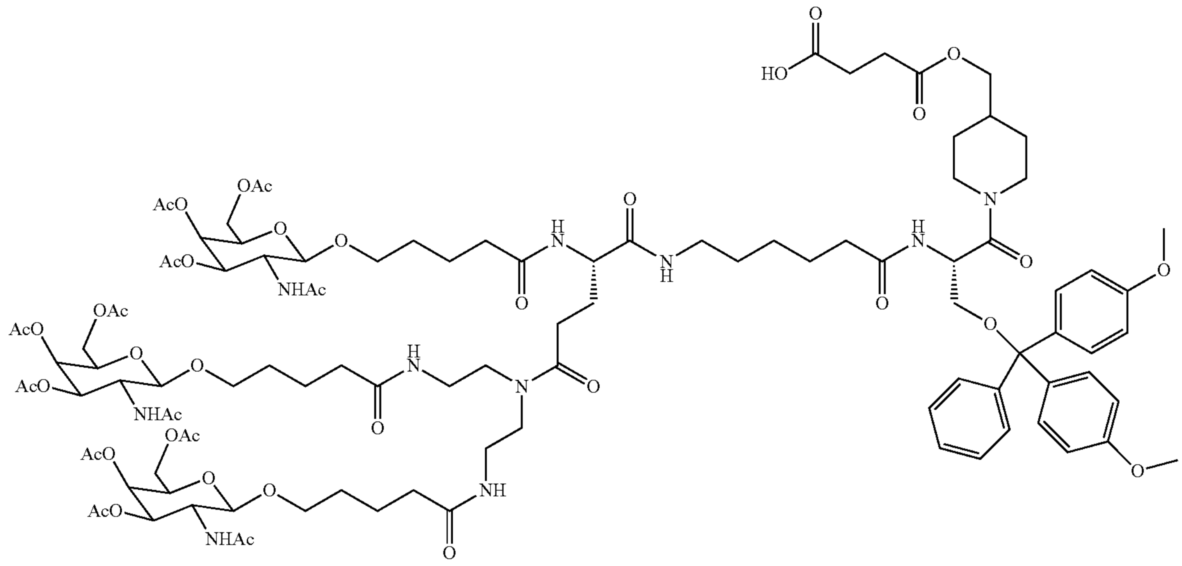 [SMILES: COc1ccc(C(OC[C@H](NC(=O)CCCCCNC(=O)[C@H](CCC(=O)N(CCNC(=O)CCCCOC2OC(COC(C)=O)C(OC(C)=O)C(OC(C)=O)C2NC(C)=O)CCNC(=O)CCCCOC2OC(COC(C)=O)C(OC(C)=O)C(OC(C)=O)C2NC(C)=O)NC(=O)CCCCOC2OC(COC(C)=O)C(OC(C)=O)C(OC(C)=O)C2NC(C)=O)C(=O)N2CCC(COC(=O)CCC(=O)O)CC2)(c2ccccc2)c2ccc(OC)cc2)cc1]

To a solution of [5-acetamido-6-[5-[2-[[(4S)-4-[5-[3-acetamido-4,5-diacetoxy-6-(acetoxymethyl)tetrahydropyran-2-yl]oxypentanoylamino]-5-[[6-[[(1S)-1-[[bis(4-methoxyphenyl)-phenyl-methoxy]methyl]-2-[4-(hydroxymethyl)-1-piperidyl]-2-oxo-ethyl]amino]-6-oxo-hexyl]amino]-5-oxo-pentanoyl]-[2-[5-[3-acetamido-4,5-diacetoxy-6-(acetoxymethyl)tetrahydropyran-2-yl]oxypentanoylamino]ethyl]amino]ethylamino]-5-oxo-pentoxy]-3,4-diacetoxy-tetrahydropyran-2-yl]methyl acetate (1.194 g, 0.56 mmol) in DCM (11 mL) is added succinic anhydride (113 mg, 1.13 mmol), TEA (0.4 mL, 3 mmol) and DMAP (213 mg, 1.69 mmol). The mixture is stirred at ambient temperature for 1 hour. After this time, the mixture is diluted with saturated $NH_4Cl$ (200 mL) and extracted with DCM (3×200 mL) and 3:1 $CHCl_3$:IPA (200 mL). The organic layers are combined, dried over sodium sulfate, filtered, and concentrated in vacuo. The resulting residue is purified by silica gel flash chromatography eluting with 0-40% MeOH/DCM and the resulting product is dried in a vacuum oven at 40° C. for 3 hours to give the title compound (1.081 g, 86%). ES/MS m/z 1109.60 (M−2H)/2.

Preparation 36

Resin Loading

A solution of 4-[[1-[(2S)-2-[6-[[(2S)-2-[5-[3-acetamido-4,5-diacetoxy-6-(acetoxymethyl)tetrahydropyran-2-yl]oxy-pentanoylamino]-5-[bis[2-[5-[3-acetamido-4,5-diacetoxy-6-(acetoxymethyl)tetrahydropyran-2-yl]oxypentanoylamino]ethyl]amino]-5-oxo-pentanoyl]amino]hexanoylamino]-3-[bis(4-methoxyphenyl)-phenyl-methoxy]propanoyl]-4-piperidyl]methoxy]-4-oxo-butanoic acid (1.00 g, 0.61 mmol) in MeCN (6 mL) and DCM (1 mL) is transferred to a resin loading cartridge. To the vessel are added 2-(1H-benzotriazol-1-yl)-1,1,3,3-tetramethyluronium hexafluorophosphate (386 mg, 0.97 mmol) and DIEA (0.25 mL, 0.48 mmol) and the cartridge is shaken at ambient temperature for 5 minutes. After this time, 1000 Å LCAA controlled-pore glass resin (5.39 g, 90 μmol/g loading, purchased from ChemGenes) is added and the mixture is shaken at ambient temperature for 18 hours. After this time, the cartridge is drained by suction and the resin is washed by shaking with DCM (10 mL) for 10 minutes. The cartridge is drained and the washing and draining procedure is repeated with 10% MeOH/DCM (10 mL) and $Et_2O$ (10 mL). After draining, a solution of acetic anhydride (6.4 mL), pyridine (20 mL) and TEA (0.22 mL) is added and the cartridge is shaken for 2 hours. After this time, the cartridge is drained and the washing and draining procedure above is repeated using DCM (10 mL), 10% MeOH/DCM (10 mL) and diethyl

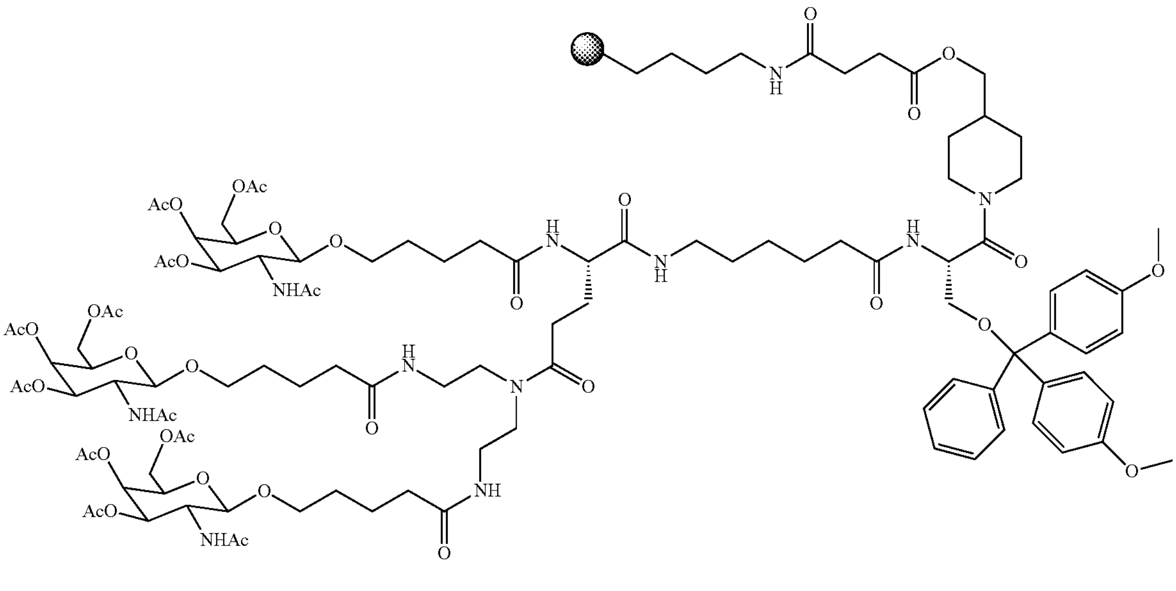 [SMILES: CCCCCNC(=O)CCC(=O)OCC1CCN(C(=O)[C@H](COC(c2ccccc2)(c2ccc(OC)cc2)c2ccc(OC)cc2)NC(=O)CCCCCNC(=O)[C@H](CCC(=O)N(CCNC(=O)CCCCOC2OC(COC(C)=O)C(OC(C)=O)C(OC(C)=O)C2NC(C)=O)CCNC(=O)CCCCOC2OC(COC(C)=O)C(OC(C)=O)C(OC(C)=O)C2NC(C)=O)NC(=O)CCCCOC2OC(COC(C)=O)C(OC(C)=O)C(OC(C)=O)C2NC(C)=O)CC1]

ether (10 mL). After draining, the resin is dried under vacuum for 30 minutes. The resin loading is determined using a standard trityl assay. The resin loading was calculated to be 34.7 μmol/g.

Preparation 37

Benzyl 2-[2-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl) tetrahydropyran-2-yl]oxypentanoylamino] pentanoylamino]ethyl]amino]-5-oxo-pentanoyl] amino]ethoxy]acetate

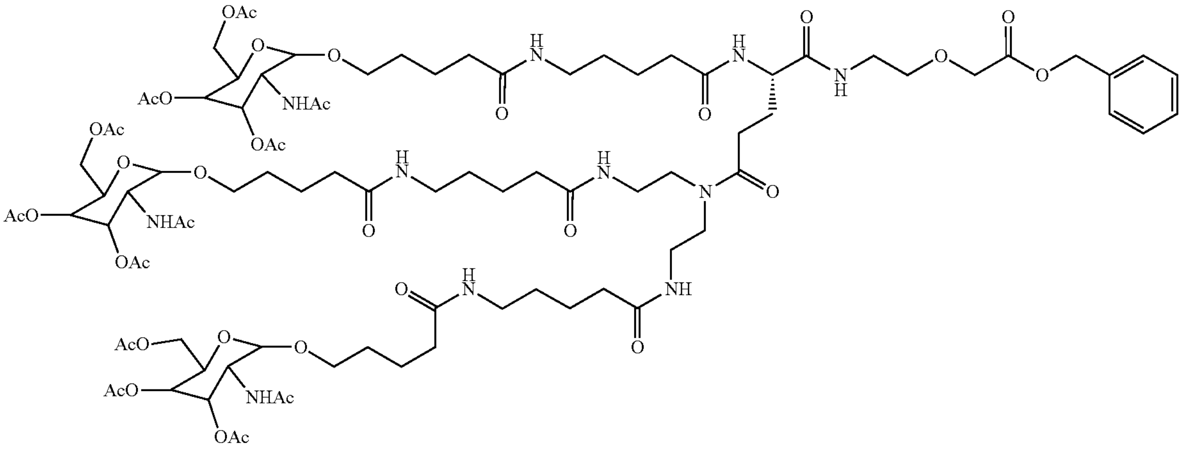 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)NCCOCC(=O)OCc2ccccc2)OC(COC(C)=O)C(OC(C)=O)C1OC(C)=O]

The title compound is prepared from (2S)-2-[5-[5-[3-Acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl) tetrahydropyran-2-yl]oxypentanoylamino]pentanoylamino] ethyl]amino]-5-oxo-pentanoic acid and benzyl 2-(2-aminoethoxy)acetate hydrochloride in a manner essentially analogous to the method of preparation 10. ES/MS m/z 1005.2 (M+2H/2).

Preparation 38

2-[2-[[(2S)-2-[5-[5-[3-Acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl) tetrahydropyran-2-yl]oxypentanoylamino] pentanoylamino]ethyl]amino]-5-oxo-pentanoyl] amino]ethoxy]acetic acid

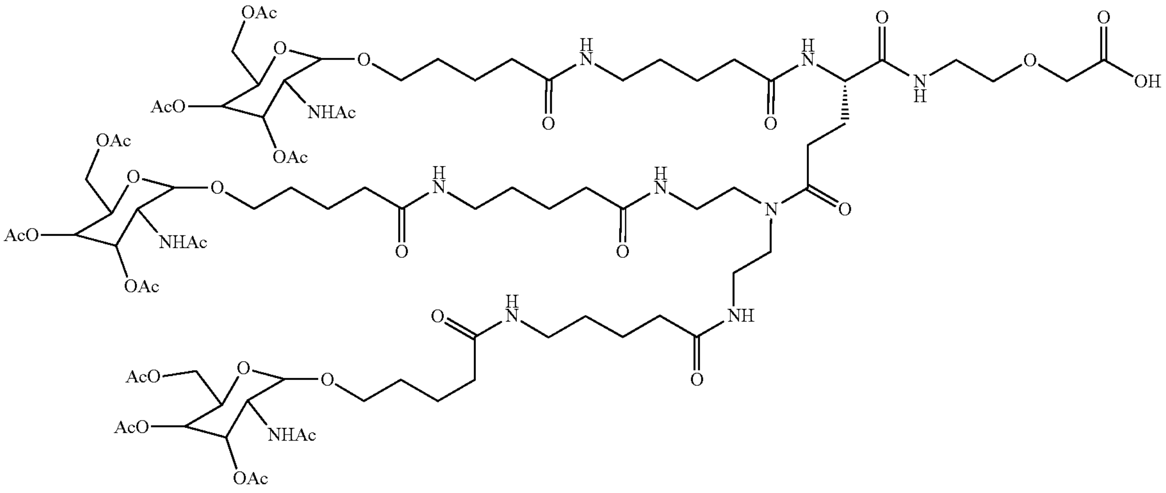 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)NCCOCC(=O)O)OC(COC(C)=O)C(OC(C)=O)C1OC(C)=O]

Benzyl 2-[2-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]ethoxy]acetate (0.120 mmol, 240 mg) is combined with 5% Pd/C (1.17 mmol, 124 mg) in MeOH (12.0 ml). The mixture is hydrogenated on a Parr shaker (ambient temperature, 10 psi) for 48 minutes, filtered through diatomaceous earth, and concentrated in vacuo to give the title compound as a gray solid (187 mg, 82%). ES/MS m/z 960.0 (M+2H/2).

Preparation 39

(2,3,5,6-Tetrafluorophenyl) 2-[2-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]ethoxy]acetate

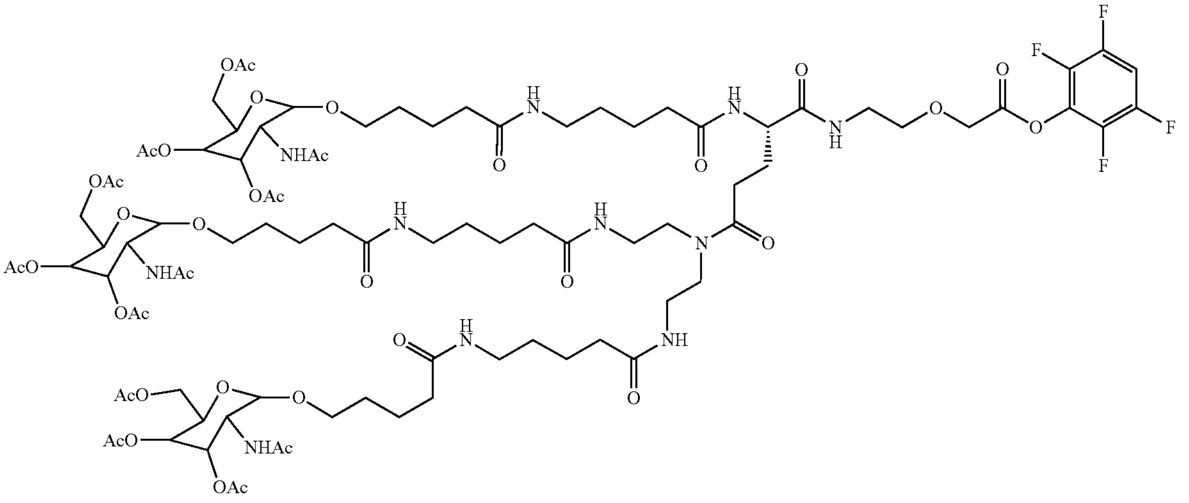 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)NCCOCC(=O)Oc2c(F)c(F)cc(F)c2F)OC(COC(C)=O)C(OC(C)=O)C1OC(C)=O]

To 2-[2-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]ethoxy]acetic acid (0.096 mmol, 184 mg) and DIEA (0.765 mmol, 140 uL) in DCM (3.0 ml) is added (2,3,5,6-tetrafluorophenyl) 2,2,2-trifluoroacetate (0.383 mmol, 100 mg) to the mixture dropwise. The mixture is stirred at ambient temperature for 16 hours. The reaction mixture is purified directly by silica gel flash chromatography eluting with 0% to 50% MeOH/DCM to give the title compound as a tan solid (197 mg, 99%). ES/MS m/z 1034.0 (M+2H/2).

Preparation 40

Benzyl 2-[2-[2-[2-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]ethoxy]ethoxy]ethoxy]acetate

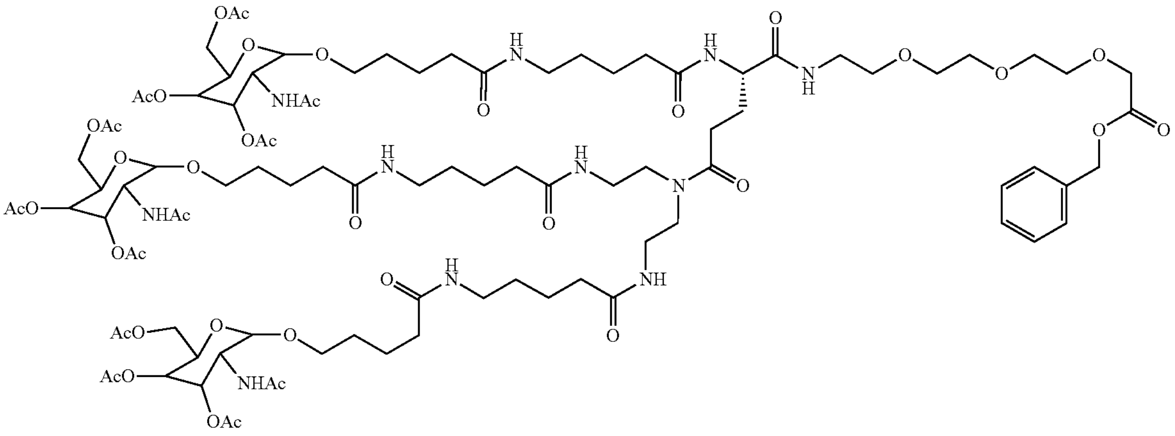 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)NCCOCCOCCOCC(=O)OCc2ccccc2)OC(COC(C)=O)C(OC(C)=O)C1OC(C)=O]

The title compound is prepared from (2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoic acid and benzyl 2-[2-[2-(2-aminoethoxy)ethoxy]ethoxy]acetate hydrochloride in a manner essentially analogous to the method of preparation 10. ES/MS m/z 1049.0 (M+2H/2).

Preparation 41

2-[2-[2-[2-[[(2S)-2-[5-[5-[3-Acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl]oxypentanoylamino]pentanoylamino]ethyl]amino]-5-oxo-pentanoyl]amino]ethoxy]ethoxy]ethoxy]acetic acid

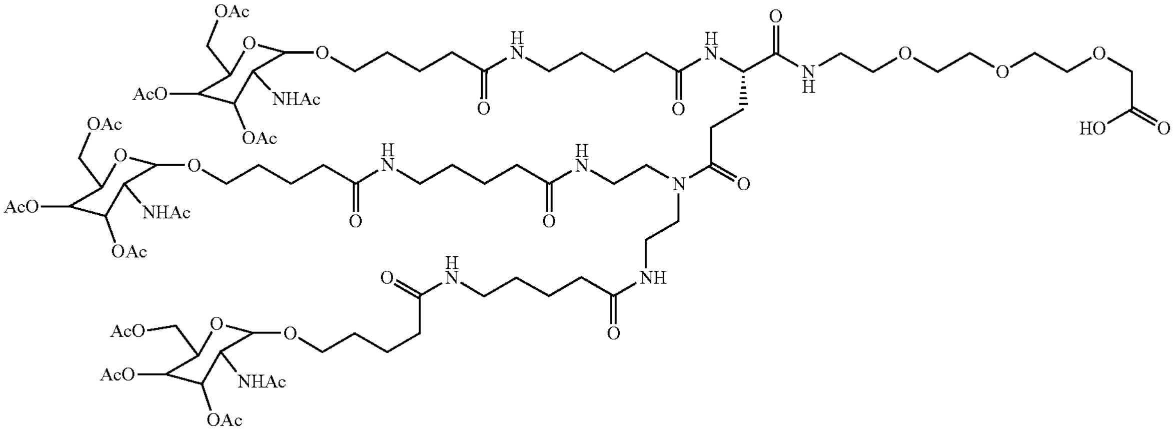 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)NCCOCCOCCOCC(=O)O)OC(COC(C)=O)C(OC(C)=O)C1OC(C)=O]

Benzyl 2-[2-[2-[2-[[(2S)-2-[5-[5-[3-acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl] oxypentanoylamino]pentanoylamino]ethyl]amino]-5-oxo-pentanoyl]amino]ethoxy]ethoxy]ethoxy]acetate (0.118 mmol, 247 mg) is combined with 5% Pd/C (1.17 mmol, 124 mg) in MeOH (12.0 mL). The mixture is hydrogenated on a Parr shaker (ambient temperature, 10 psi) for 1 hour, filtered through diatomaceous earth, and concentrated in vacuo to give the title compound as a gray solid (227 mg, 96%). ES/MS m/z 1004.0 (M+2H/2).

Preparation 42

(2,3,5,6-Tetrafluorophenyl) 2-[2-[2-[2-[[(2S)-2-[5-[5-[3-acetamido-4,5-diacetoxy-6-(acetoxymethyl) tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl] oxypentanoylamino]pentanoylamino]ethyl]amino]-5-oxo-pentanoyl]amino]ethoxy]ethoxy]ethoxy] acetate

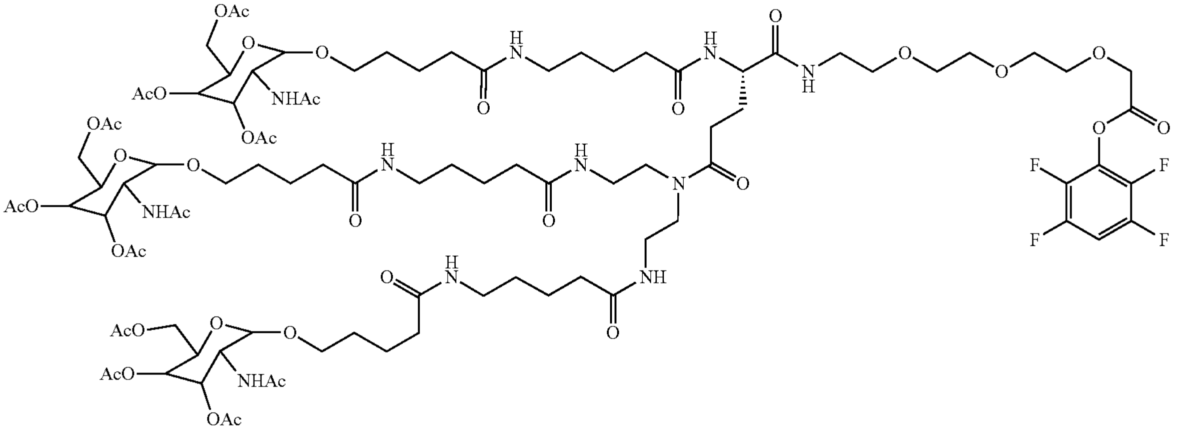 [SMILES: CC(=O)NC1C(OCCCCC(=O)NCCCCC(=O)NCCN(CCNC(=O)CCCCNC(=O)CCCCOC2OC(COC(C)=O)C(OC(C)=O)C(OC(C)=O)C2NC(C)=O)C(=O)CC[C@H](NC(=O)CCCCNC(=O)CCCCOC2OC(COC(C)=O)C(OC(C)=O)C(OC(C)=O)C2NC(C)=O)C(=O)NCCOCCOCCOCC(=O)Oc2c(F)c(F)cc(F)c2F)OC(COC(C)=O)C(OC(C)=O)C1OC(C)=O]

To 2-[2-[2-[2-[[(2S)-2-[5-[5-[3-Acetamido-4,5-diacetoxy-6-(acetoxymethyl)tetrahydropyran-2-yl]oxypentanoylamino]pentanoylamino]-5-[bis[2-[5-[5-[3-acetamido-4,5-diacetoxy-6-(acetoxymethyl)tetrahydropyran-2-yl] oxypentanoylamino]pentanoylamino]ethyl]amino]-5-oxo-pentanoyl]amino]ethoxy]ethoxy]ethoxy]acetic acid (0.111 mmol, 222 mg) and DIEA (0.883 mmol, 154 uL) in DCM (3.0 ml) is added (2,3,5,6-tetrafluorophenyl) 2,2,2-trifluoroacetate (0.443 mmol, 116 mg) to the mixture dropwise. The mixture is stirred at ambient temperature for 16 hours. The reaction mixture is purified directly by silica gel flash chromatography eluting with 0% to 50% MeOH/DCM to give the title compound as a tan solid (174 mg, 73%). ES/MS m/z 1078.2 (M+2H/2).

EXAMPLE 1

Conjugation Protocol

For the synthesis of GalNAc-conjugated sense strands, a sense strand with a 3' C6-$NH_2$ functional group is first synthesized using standard phosphoramidite chemistry. A stock solution of GalNAc ligand-NHS ester (10 mmol/L in acetonitrile; 1 eq) is prepared. Borate buffer (10% v/v; 20×) is added to oligonucleotide C6-$NH_2$ sense strand in an Eppendorf tube, then GalNAc ligand (5 eq) is added. The mixture is shaken at ambient temperature for 16 hours. After this time, the mixture is transferred to a 15 mL falcon tube, ammonium hydroxide (28 mass %) is added, and the mixture is shaken at ambient temperature for 2 hours. The ammonia is then removed in vacuo. The residue is purified by ion-exchange chromatography. Conditions: Solvent A: 15% MeCN/20 mM $NaH_2PO_4$, Solvent B: 15% MeCN/20 mM $NaH_2PO_4$, 1M NaBr; 35-55% B over 5 CV at 8 mL/min, column temperature 60° C. The desired fractions are pooled and desalted by spin-filtration using an Eppendorf centrifuge or desalting column. After desalting, the material is recovered and OD and volume are measured to obtain concentration.

Alternatively, conjugation is to the 5' position of the sense strand through immobilizing the GalNAc ligand on microporous polystyrene resin or controlled pore glass and synthesizing using established solid phase oligonucleotide synthesis methods with 5'-CE ß-cyanoethyl) phosphoramidites.

Alternatively, the GalNAc ligand is converted to a suitable phosphoramidite and delivered to the 5' position of the sense strand using standard phosphoramidite chemistry.

EXAMPLE 2: ANNEALING

To generate the siRNA duplexes of a sense and antisense strand, the following procedures are performed. To a falcon tube containing oligonucleotide sense strand-GalNAc conjugate, the corresponding antisense oligonucleotide (1 eq) is added and vortexed for 10 seconds before spin-filtering through 100K MWCO Amicon filter unit to remove particulates. The filtrate is recovered and concentrated in vacuo on a Genevac evaporator. The residue is reconstituted in 1×PBS, filtered through 0.2 μfilter, and OD and volume are measured to obtain concentration.

An endotoxin test is performed using a Limulus amebocyte lysate on an Endosafe®-nexgen PTS instrument.

TABLE 1
| Exemplary molecules synthesized utilizing the aforementioned conjugation and annealing protocols. | | |
|---|---|---|
| Molecule Identifier | Ligand attached to 3' of sense strand | siRNA |
| 1 | 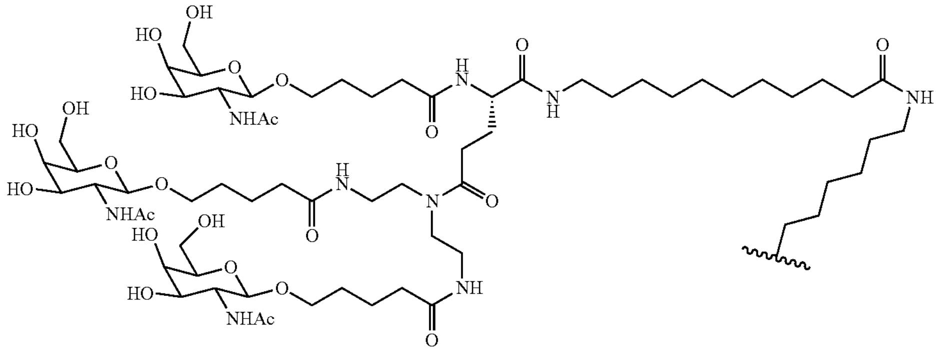 [SMILES: *CCCCCCNC(=O)CCCCCCCCCCNC(=O)[C@H](CCC(=O)N(CCNC(=O)CCCCOC1OC(CO)C(O)C(O)C1NC(C)=O)CCNC(=O)CCCCOC1OC(CO)C(O)C(O)C1NC(C)=O)NC(=O)CCCCOC1OC(CO)C(O)C(O)C1NC(C)=O] | LDHA |
| 2 | 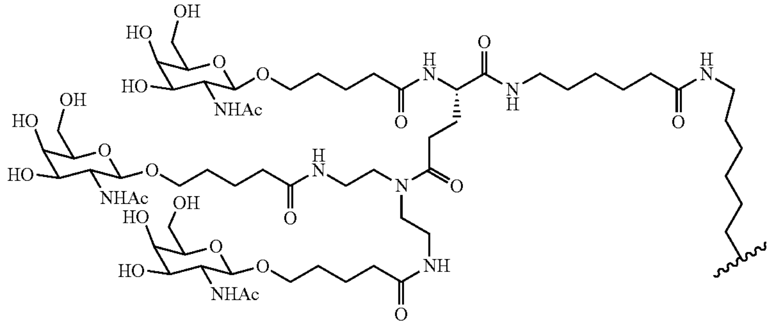 [SMILES: *CCCCCCNC(=O)CCCCCNC(=O)[C@H](CCC(=O)N(CCNC(=O)CCCCOC1OC(CO)C(O)C(O)C1NC(C)=O)CCNC(=O)CCCCOC1OC(CO)C(O)C(O)C1NC(C)=O)NC(=O)CCCCOC1OC(CO)C(O)C(O)C1NC(C)=O] | LDHA |
| 3 | 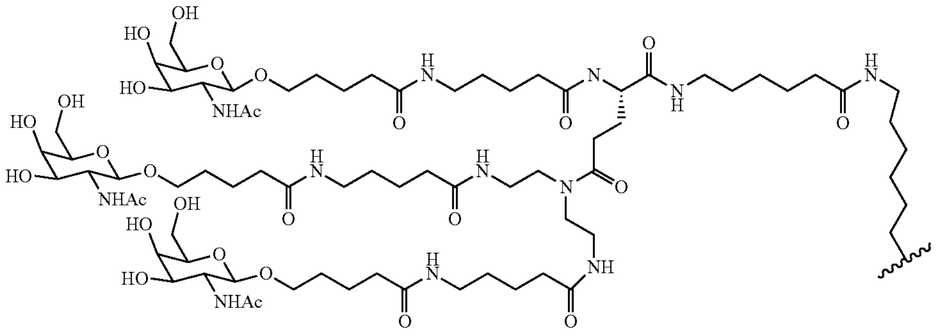 [SMILES: *CCCCCCNC(=O)CCCCCNC(=O)[C@H](CCC(=O)N(CCNC(=O)CCCCNC(=O)CCCCOC1OC(CO)C(O)C(O)C1NC(C)=O)CCNC(=O)CCCCNC(=O)CCCCOC1OC(CO)C(O)C(O)C1NC(C)=O)NC(=O)CCCCNC(=O)CCCCOC1OC(CO)C(O)C(O)C1NC(C)=O] | LDHA |

TABLE 1-continued

Exemplary molecules synthesized utilizing the aforementioned conjugation and annealing protocols.

| Molecule Identifier | Ligand attached to 3' of sense strand | siRNA |
|---|---|---|
| 4 | 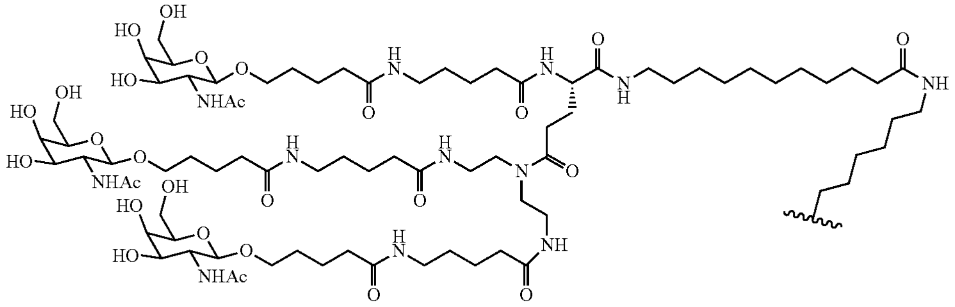 [SMILES: *CCCCCCNC(=O)CCCCCCCCCCNC(=O)[C@H](CCC(=O)N(CCNC(=O)CCCCNC(=O)CCCCOC1OC(CO)C(O)C(O)C1NC(C)=O)CCNC(=O)CCCCNC(=O)CCCCOC1OC(CO)C(O)C(O)C1NC(C)=O)NC(=O)CCCCNC(=O)CCCCOC1OC(CO)C(O)C(O)C1NC(C)=O] | LDHA |
| 5 | 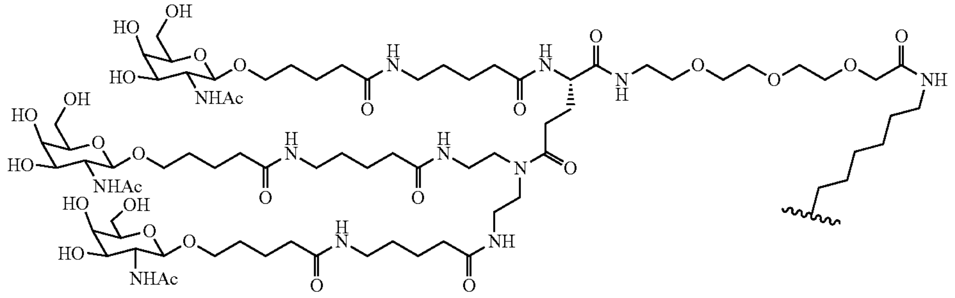 [SMILES: *CCCCCCNC(=O)COCCOCCOCCNC(=O)[C@H](CCC(=O)N(CCNC(=O)CCCCNC(=O)CCCCOC1OC(CO)C(O)C(O)C1NC(C)=O)CCNC(=O)CCCCNC(=O)CCCCOC1OC(CO)C(O)C(O)C1NC(C)=O)NC(=O)CCCCNC(=O)CCCCOC1OC(CO)C(O)C(O)C1NC(C)=O] | LDHA |
| 6 | 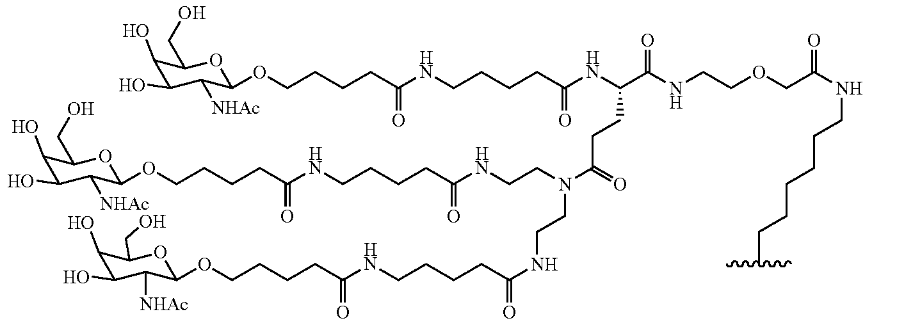 [SMILES: *CCCCCCNC(=O)COCCNC(=O)[C@H](CCC(=O)N(CCNC(=O)CCCCNC(=O)CCCCOC1OC(CO)C(O)C(O)C1NC(C)=O)CCNC(=O)CCCCNC(=O)CCCCOC1OC(CO)C(O)C(O)C1NC(C)=O)NC(=O)CCCCNC(=O)CCCCOC1OC(CO)C(O)C(O)C1NC(C)=O] | LDHA |

EXAMPLE 3: GENERAL PROCEDURE FOR OLIGO SYNTHESIS USING GALNAC-FUNCTIONALIZED CPG

Oligo synthesis is conducted on a Mermade 12 instrument using phosphoramidite chemistry. Sense strands are synthesized from the prefunctionalized GalNAc solid support and antisense strands are synthesized using standard support preloaded with the first nucleotide of the oligo sequence. Oligos are cleaved and deprotected using concentrated ammonium hydroxide solution (28% by mass) and purified by ion exchange chromatography using conditions described above. Desalting, annealing and endotoxin testing are conducted as described above.

| Gene | Antisense 5' to 3' | Sense 5' to 3' |
|---|---|---|
| HPRT | [Phos]mA*fU*mAmAmAfAmUmCmUmAmCmAmGfUmCfAmUmAmGmGmA*mA*mU | mU*mC*mCmUmAmUfGmAfCfUfGmUmAmGmAmUmUmUmU*mA*mU |
| LDHA | [Phos]mA*fC*mGmUmAfGmGmUmCmAmAmGmAfUmAfUmCmCmAmCmU*mG*mG | mA*mG*mUmGmGmAfUmAfUfCfUmUmGmAmCmCmUmAmC*mG*mU |
| DPP4 | [Phos]mA*fA*mUmAmAfGmGmAmGmGmUmAmCfUmCfAmAmCmUmUmG*mU*mU | mC*mA*mAmGmUmUfGmAfGfUfAmCmCmUmCmCmUmUmA*mU*mU |

Key - [Phos] indicates a phosphorylated 5' residue; m indicates a 2' O-Me group on the ribose on the nucleotide/nucleoside base that is written immediately following the m; f indicates a 2' Fluoro group on the ribose on the nucleotide/nucleoside base that is written immediately following the f; and * indicates a modified bond that is phosphorothioate (PS)

EXAMPLE 4
TABLE 2
| Exemplary molecules synthesized utilizing the aforementioned procedure for oligo synthesis using GalNAc-functionalized CPG and annealing protocols. | | |
|---|---|---|
| Mole-cule Iden-tifier | Ligand attached to 3' of sense strand | siRNA |
| 7 | 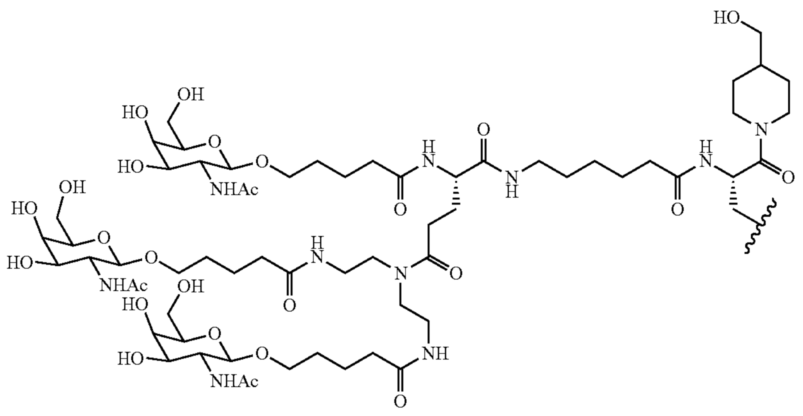 [SMILES: *C[C@H](NC(=O)CCCCCNC(=O)[C@H](CCC(=O)N(CCNC(=O)CCCCOC1OC(CO)C(O)C(O)C1NC(C)=O)CCNC(=O)CCCCOC1OC(CO)C(O)C(O)C1NC(C)=O)NC(=O)CCCCOC1OC(CO)C(O)C(O)C1NC(C)=O)C(=O)N1CCC(CO)CC1] | HPRT |
| 8 | 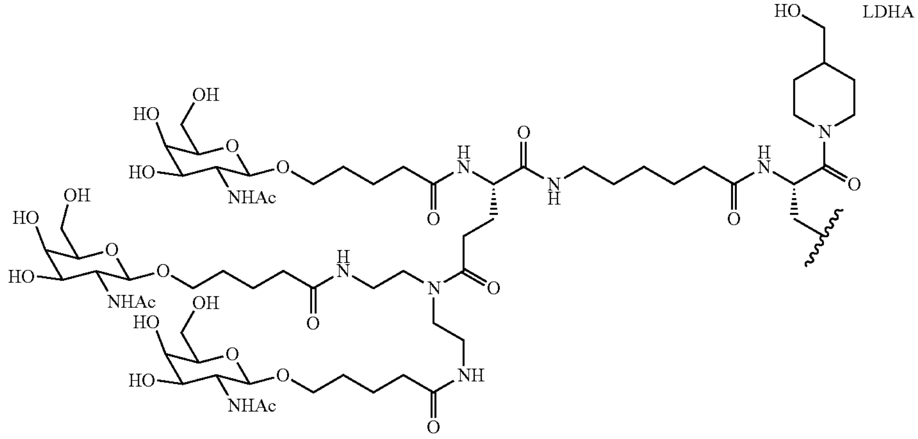 | LDHA |
| 9 | 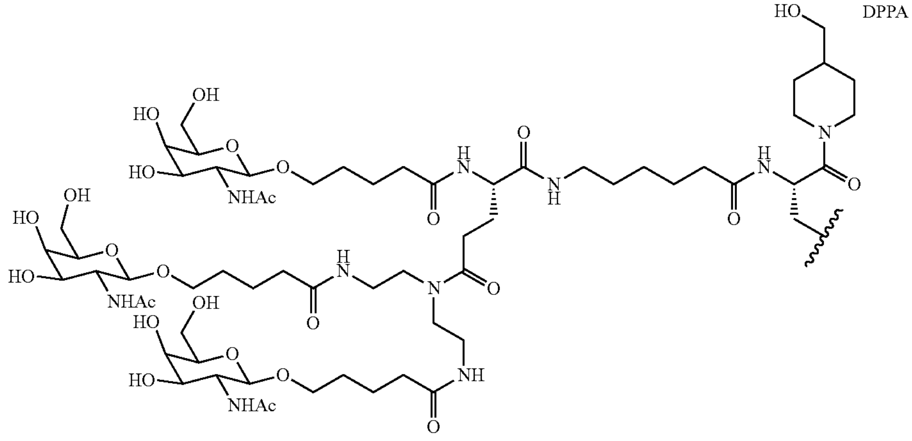 | DPPA |

EXAMPLE 5

TABLE 3

| GalNAc controls | | |
|---|---|---|
| Molecule Identifier | Ligand attached to 3' of sense strand | siRNA |
| GalNAc control I | 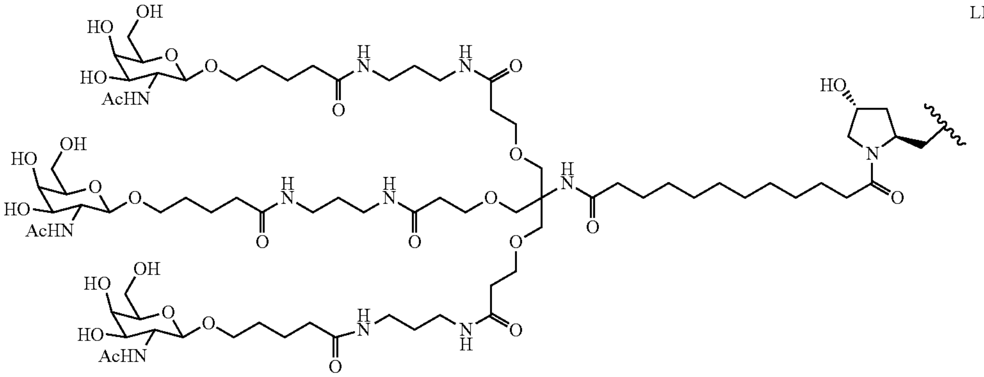 | LDHA |
| GalNAc control II | 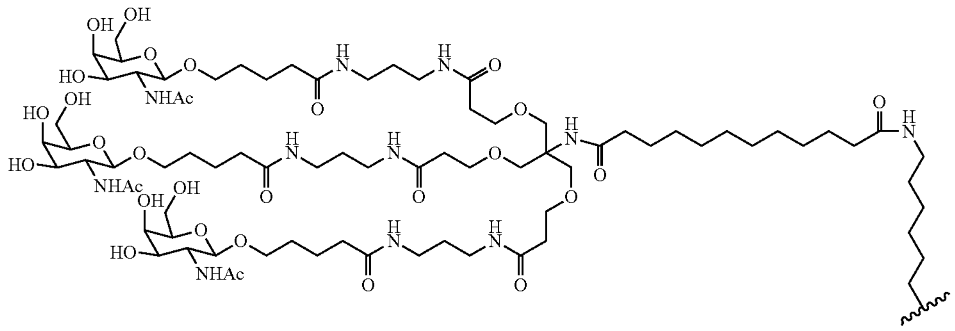 [SMILES: *CCCCCCNC(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O] | LDHA |

EXAMPLE 6: BIOLOGICAL ASSAYS

Evaluation of GalNAc-LDHA siRNA Conjugates Gene Knock-Down In Vivo

Animals

All animals are individually housed in a temperature-controlled facility (24° C.) with a 12 hr/12 hr light/dark cycle. Animal protocols are approved by the Eli Lilly and Company IACUC. Male, approximately 8 weeks old, C57BL/6 mice (Envigo) are weighed and randomized by body weight into treatment groups of 6 animals per group. Animals are treated with either PBS or siRNA conjugate via subcutaneous injection. Fourteen days post dose, animals are sacrificed and liver tissues are rapidly dissected and flash-frozen in liquid nitrogen.

RNA Isolation and Real-Time Quantitative RT-PCR

Total RNA is isolated from liver samples using TRIzol reagent (Ambion) and PureLink Pro 96 total RNA purification kit (Invitrogen). One microgram of RNA is used to synthesize cDNA using a High-Capacity cDNA Reverse Transcription kit (Applied Biosystems). Quantitative real-time PCR is performed on an Applied Biosystems QuantStudio 7 Flex Real-Time PCR systems (Applied Biosystems). CT values are normalized to RPLP0 (Mm01974474_gH, Applied Biosystems) and relative expression for LDHA (Mm03646738_gI, Applied Biosystems) are calculated by the ΔΔCT method. Fold change is calculated by normalizing relative expression to vehicle-treated animals.

TABLE 4

| Knockdown of LDHA mRNA in mouse primary hepatocytes | | |
|---|---|---|
| Example | Rel IC50 (nM) | % Rel Max |
| 1 | 4.01 (1.30, n = 2) | 95.0 (0.00, n = 2) |
| 2 | 2.30 (0.0105, n = 2) | 95.3 (0.354, n = 2) |
| 3 | 2.21 (0.313, n = 2) | 96.9 (0.547, n = 2) |
| 4 | 3.89 (3.11, n = 2) | 95.7 (0.155, n = 2) |
| 5 | 1.70 (0.0561, n = 2) | 97.1 (1.02, n = 2) |
| 6 | 1.47 (0.251, n = 2) | 98.3 (0.320, n = 2) |
| GalNAc control I | 1.85 (0.218, n = 2) | 99.7 (0.128, n = 2) |
| GalNAc control II | 4.70 (1.77, n = 2) | 96.0 (0.00, n = 2) |

TABLE 5

| In vivo knockdown data | | |
|---|---|---|
| Example | Ave % KD | Std Error |
| 1 | 52.6 | 5.52 |
| 2 | 76.4 | 1.21 |
| 3 | 55.7 | 3.09 |
| 4 | 52.7 | 5.46 |

TABLE 5-continued

| In vivo knockdown data | | |
|---|---|---|
| Example | Ave % KD | Std Error |
| 5 | 56.2 | 4.11 |
| 6 | 51.5 | 4.30 |
| GalNAc control I | 41.2 | 2.29 |
| GalNAc control II | 42.8 | 7.70 |

GalNAc-LDHA siRNA 24-Hour Tissue Exposure Screen

Animals

All animals are individually housed in a temperature-controlled facility (24° C.) with a 12 hr/12 hr light/dark cycle. Animal protocols are approved by the Eli Lilly and Company IACUC. Male, approximately 8 weeks old, C57BL/6 mice (Envigo) are weighed and randomized by body weight into treatment groups of 5 animals per group. Animals are treated with either PBS vehicle or siRNA conjugate via subcutaneous injection. Twenty-four hours post dose, animals are sacrificed, plasma samples are collected via cardiac puncture bleed and liver/kidney tissues are rapidly dissected and flash-frozen in liquid nitrogen. Tissue concentrations of siRNA and metabolites are determined by PNA hybridization and anion-exchange high performance liquid chromatography analysis coupled to fluorescence detection.

TABLE 6

| Liver exposure | | | | |
|---|---|---|---|---|
| Example | Ave 5' OH metabolite (ng/g) | StdError 5'OH metabolite (ng/g) | Ave 5' n-1 metabolite (ng/g) | StdError 5' n-1 metabolite (ng/g) |
| 1 | 4299.1 | 825.6 | 2,095.9 | 382.5 |
| 2 | 9809.5 | 1,199.8 | 5,074.1 | 559.3 |
| 3 | 3786.9 | 417.5 | 2,272.2 | 242.3 |
| 4 | 3847.0 | 439.6 | 1,973.7 | 187.6 |
| 5 | 5480.4 | 1,042.9 | 3,285.7 | 611.2 |
| 6 | 5079.1 | 569.8 | 3,059.2 | 340.6 |
| GalNAc control I | 6258.6 | 797.23 | 3729.3 | 441.2 |
| GalNAc control II | 3723.2 | 526.2 | 2019.3 | 301.2 |

TABLE 7

| Kidney Exposure | | | | |
|---|---|---|---|---|
| Example | Avg 5' OH metabolite (ng/g) | StdError 5'OH metabolite (ng/g) | Avg 5' n-1 metabolite (ng/g) | StdError 5' n-1 metabolite (ng/g) |
| 1 | 396.1 | 21.7 | 195.3 | 10.8 |
| 2 | 144.3 | 7.9 | 47.3 | 3.9 |
| 3 | 121.6 | 47.8 | 47.6 | 21.9 |
| 4 | 247.5 | 46.5 | 107.6 | 22.9 |
| 5 | 293.6 | 21.5 | 115.8 | 9.1 |
| 6 | 315.4 | 15.5 | 123.2 | 5.5 |
| GalNAc control I | 1334.4 | 87.8 | 586.8 | 41.3 |
| GalNAc control II | 285 | 42.6 | 134.5 | 25.4 |

EXAMPLE 7: IN VITRO KNOCKDOWN OF MOUSE GENES

Mouse primary hepatocytes (MPH) are freshly isolated and plated on Corning plates at 15k per well and siRNA conjugates in PBS are added to each well. Dose response experiments are performed using 1000, 333, 111, 37, 12, 4, 1.37, 0.46, 0.15, 0.05, and 0.017 nM final GalNAc-conjugated duplex concentration in mouse primary hepatocytes.

RNA is isolated directly from the plated cells using Quick-RNA 96 Kit from Zymo Research. The final purified and eluted RNA is used immediately or stored frozen. cDNA is synthesized from the purified RNA using the Fast Advanced RT Master Mix from Invitrogen and a QuantStudio 7 Flex Real-Time PCR System (Life Technologies), incubating 37° C. for 30 minutes, 95° C. for 5 minutes, and a 4° C. hold. The cDNA is used to perform RealTime PCR using a QuantStudio 7 Flex Real-Time PCR System (Life Technologies) using the following parameters: 50° C. for 2 minutes, 95° C. for 10 minutes, 40 cycles of 95° C. for 15 seconds and 60° C. for 1 minute.

Results of the RT-PCR assay for the following mouse target genes HPRT, LDHA, and DPP4 (Life Technologies) and IC50 calculations are shown in Table 8. Knock-down levels represent relative knockdown as compared to vehicle alone, and are further normalized to mouse Rplp0 (Life Technologies) in order to compare across samples. $IC_{50}$ are calculated using a 4-parameter fit model using XLFit. These results demonstrate effective knockdown of the delivery moiety disclosed herein, with 80-97% knockdown of three different genes.

TABLE 8

| $IC_{50}$ and maximum percent knockdown data in mouse primary hepatocytes with siRNAs conjugated to the novel delivery moiety comprising GalNAc disclosed herein (%) | | | |
|---|---|---|---|
| Example | Duplex ID | $IC_{50}$ (nM) | Max knockdown (%) |
| 7 | HPRT-GalNAc1 | 1.9 | 97.17 |
| 8 | LDHA-GalNAc1 | 6.03 | 99.54 |
| 9 | DPP4-GalNAc1 | 4.79 | 81.8 |

We claim:

1. A compound comprising Formula I conjugated to R:

Formula I

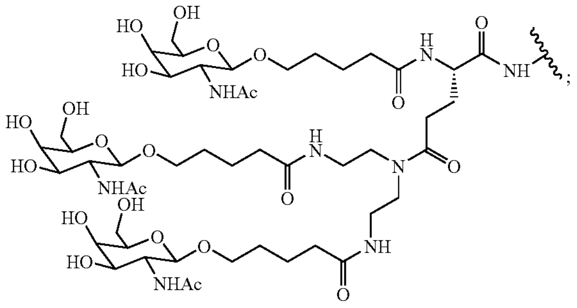

wherein R is optionally conjugated to Formula I via a linker, and wherein R comprises an antisense strand, and wherein the antisense strand comprises a region of complementarity to a gene of interest, and wherein the antisense strand is 15 to 40 nucleotides in length.

2. The compound of claim 1, wherein Formula I is conjugated to R via a linker.

3. The compound of claim 2, wherein the linker comprises a linker of Formula II having connection points A and B or the linker comprises Formula III having connection points C and D:

Formula II

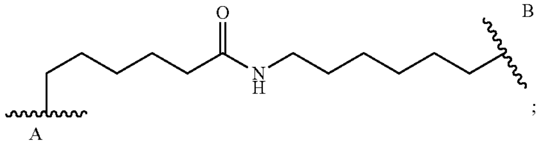

; or

Formula III

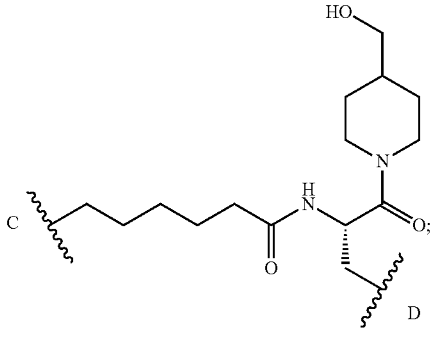

wherein connection point A or connection point C are conjugated to Formula I.

4. The compound of claim 2, wherein the linker further comprises a phosphate group at connection point B or connection point D, and wherein the phosphate group is conjugated to R.

5. The compound of claim 2, wherein the linker comprises a linker of Formula III having connection points C and D:

Formula III

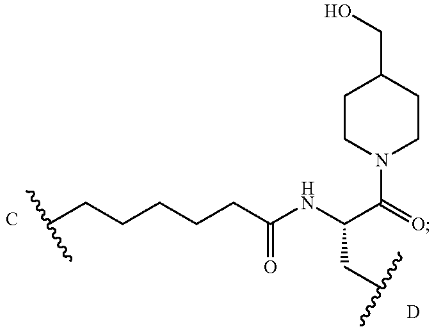

wherein connection point C is conjugated to Formula I.

6. The compound of claim 1, wherein the region of complementarity to the gene of interest is at least 15 contiguous nucleotides in length.

7. The compound of claim 6, wherein R further comprises a sense strand, and wherein the sense strand and the antisense strand form a region of complementarity of at least 15 nucleotides in length.

8. The compound of claim 7, wherein Formula I is conjugated to the sense strand or the antisense strand.

9. The compound of claim 7, wherein Formula I is conjugated to the antisense strand.

10. The compound of claim 7, wherein Formula I is conjugated to the sense strand.

11. The compound of claim 10, wherein Formula I is conjugated to the 3' terminal nucleotide of the sense strand.

12. The compound of claim 7, wherein the sense strand and the antisense strand form a region of complementarity of at least 18 nucleotides in length.

13. The compound of claim 7, wherein the antisense strand forms a region of complementarity of at least 15 nucleotides with the sense strand.

14. The compound of claim 7, wherein the sense strand and antisense strand are each independently 18 to 23 nucleotides in length.

15. The compound of claim 7, wherein the sense strand and antisense strand are each independently 21 to 23 nucleotides in length.

16. The compound of claim 7, wherein the antisense strand comprises a 3' overhang of two nucleotides.

17. The compound of claim 7, wherein the sense strand or the antisense strand comprise one or more modified nucleotides.

18. The compound of claim 7, wherein the one or more modified nucleotides is a 2' Fluoro modified nucleotide, a 2'-O-methyl modified nucleotide, a 2'-O-alkyl modified nucleotide, or a O-methoxyethyl modified nucleotide.

19. The compound of claim 7, wherein the sense strand comprises one or more modified nucleotides, and wherein each of the nucleotides of the sense strand is a modified nucleotide.

20. The compound of claim 7, wherein the antisense strand comprises one or modified nucleotides and wherein each of the nucleotides of the antisense strand is a modified nucleotide.

21. The compound of claim 7, wherein the sense or the antisense strand comprise one or more modified internucleotide linkages.

22. The compound of claim 7, wherein the one or more modified internucleotide linkages is a phosphorothioate linkage.

23. The compound of claim 7, wherein the 5' nucleotide of the antisense strand is phosphorylated or comprises a phosphate analog.

24. The compound of claim 7, wherein the 5' nucleotide of the antisense strand comprises a vinylphosphonate group.

25. The compound of claim 7, wherein the sense strand and the antisense strand are an siRNA.

26. A compound comprising Formula V conjugated to R:

Formula V

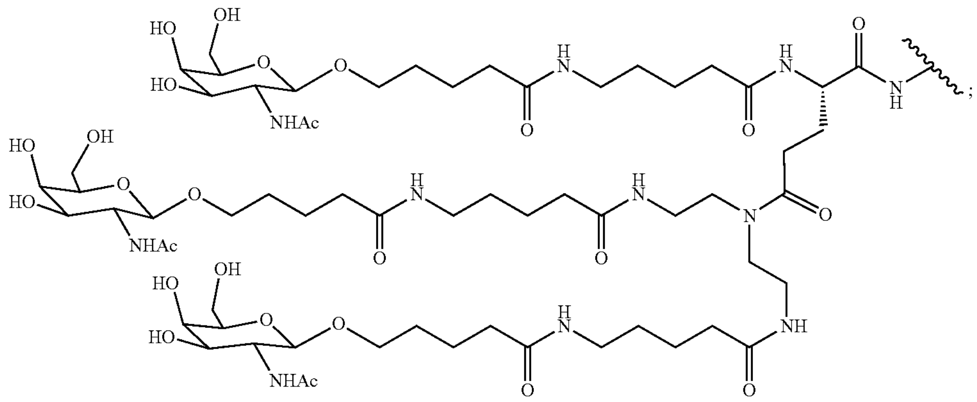

wherein R is optionally conjugated to Formula V via a linker, and wherein R comprises an antisense strand, and wherein the antisense strand comprises a region of complementarity to a gene of interest, and wherein the antisense strand is 15 to 40 nucleotides in length.

27. The compound of claim 26, wherein Formula V is conjugated to R via a linker.

28. The compound of claim 27, wherein the linker comprises a linker of Formula II having connection points A and B or the linker comprises Formula III having connection points C and D:

Formula II

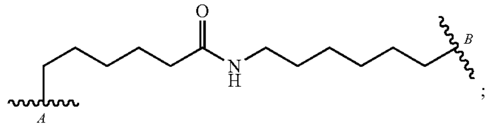

-continued

Formula III

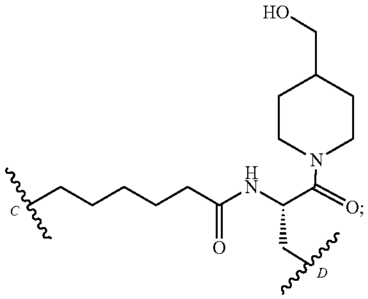

wherein connection point A or connection point C is conjugated to Formula V.

* * * * *